(12) United States Patent
Van De Maele

(10) Patent No.: US 11,759,372 B2
(45) Date of Patent: Sep. 19, 2023

(54) ABSORBENT STRUCTURE WITH PERMANENT AND TEMPORARY ATTACHMENTS

(71) Applicant: Marleen Van De Maele, Buggenhout (BE)

(72) Inventor: Marleen Van De Maele, Buggenhout (BE)

(73) Assignee: DRYLOCK TECHNOLOGIES NV, Zele. (BE)

( * ) Notice: Subject to any disclaimer, the term of this patent is extended or adjusted under 35 U.S.C. 154(b) by 906 days.

(21) Appl. No.: 15/802,769

(22) Filed: Nov. 3, 2017

(65) Prior Publication Data

US 2018/0064584 A1 Mar. 8, 2018

Related U.S. Application Data

(63) Continuation of application No. 13/879,454, filed as application No. PCT/EP2011/005139 on Oct. 13, 2011, now abandoned.

(30) Foreign Application Priority Data

| Oct. 13, 2010 | (EP) | .................................... 10447020 |
| Oct. 13, 2010 | (EP) | .................................... 10447021 |

(Continued)

(51) Int. Cl.
*A61F 13/15* (2006.01)
*A61F 13/539* (2006.01)
(Continued)

(52) U.S. Cl.
CPC .. *A61F 13/15585* (2013.01); *A61F 13/15658* (2013.01); *A61F 13/539* (2013.01);
(Continued)

(58) Field of Classification Search
CPC .... A61F 2013/15357; A61F 2013/1539; A61F 2013/15471; A61F 2013/15591;
(Continued)

(56) References Cited

U.S. PATENT DOCUMENTS

| 4,124,116 A | 11/1978 | McCabe, Jr. |
| 4,892,535 A * | 1/1990 | Bjornberg ............. A61F 13/515 604/366 |

(Continued)

FOREIGN PATENT DOCUMENTS

| EP | 0432126 A1 | 4/1999 |
| EP | 1142785 A1 | 10/2001 |

(Continued)

*Primary Examiner* — Kathryn E Ditmer
(74) *Attorney, Agent, or Firm* — Dennemeyer & Associates, LLC

(57) ABSTRACT

The present invention relates to an absorbent structure, preferably for use in absorbent products, such as used in the food, consumer, household, building and construction, beauty and medical industry, and as used in the personal hygiene industry. The substantially cellulose free absorbent structures continuously immobilise absorbent polymer material via initial smaller pockets and subsequently larger compartments allowing excellent fluid management of the absorbent polymer material in dry, partially and fully liquid loaded state. Preferably such absorbent structure volume increases are result of temporary secondary attachment patterns made in combination with substantially permanent primary attachment grids allowing the release of bigger volumes from the initial smaller volumes by detachment of the secondary attachments. Furthermore the absorbent structure according to an embodiment of the invention non-homogeneously swells to form a liquid-managing surface structure as a result of exposing the absorbent structure to liquid. The present invention foresees in the need for improved flexible, thin, lightweight absorbent structures (Continued)

which overcome the absorbency problems of the prior art during absorption, distribution and retention of liquids with optimal fit.

11 Claims, 7 Drawing Sheets

(30) Foreign Application Priority Data

| Oct. 13, 2010 | (EP) | 10447022 |
|---|---|---|
| Oct. 13, 2010 | (EP) | 10447023 |
| Oct. 13, 2010 | (EP) | 10447024 |
| Feb. 3, 2011 | (EP) | 11153268 |

(51) Int. Cl.

| A61F 13/532 | (2006.01) |
|---|---|
| A61F 13/53 | (2006.01) |
| B32B 5/16 | (2006.01) |
| B32B 3/28 | (2006.01) |
| B32B 37/24 | (2006.01) |
| B32B 5/30 | (2006.01) |
| B32B 27/12 | (2006.01) |
| B32B 7/12 | (2006.01) |
| D04H 1/46 | (2012.01) |
| B05D 1/32 | (2006.01) |
| B05C 19/04 | (2006.01) |
| B05C 1/10 | (2006.01) |
| B32B 3/08 | (2006.01) |
| B32B 5/18 | (2006.01) |
| B32B 7/02 | (2019.01) |
| B32B 27/08 | (2006.01) |
| B32B 27/32 | (2006.01) |
| B32B 5/24 | (2006.01) |
| B32B 9/04 | (2006.01) |
| B32B 27/06 | (2006.01) |
| B32B 27/10 | (2006.01) |
| B32B 29/02 | (2006.01) |
| B32B 7/08 | (2019.01) |
| B32B 9/02 | (2006.01) |
| B32B 5/02 | (2006.01) |
| B32B 3/26 | (2006.01) |
| B32B 7/04 | (2019.01) |
| B32B 5/26 | (2006.01) |
| B32B 29/00 | (2006.01) |
| B32B 37/00 | (2006.01) |

(52) U.S. Cl.
CPC ............ *A61F 13/5323* (2013.01); *B05C 1/10* (2013.01); *B05C 19/04* (2013.01); *B05D 1/32* (2013.01); *B32B 3/08* (2013.01); *B32B 3/266* (2013.01); *B32B 3/28* (2013.01); *B32B 5/022* (2013.01); *B32B 5/024* (2013.01); *B32B 5/16* (2013.01); *B32B 5/18* (2013.01); *B32B 5/245* (2013.01); *B32B 5/26* (2013.01); *B32B 5/30* (2013.01); *B32B 7/02* (2013.01); *B32B 7/04* (2013.01); *B32B 7/08* (2013.01); *B32B 7/12* (2013.01); *B32B 9/02* (2013.01); *B32B 9/04* (2013.01); *B32B 9/045* (2013.01); *B32B 9/047* (2013.01); *B32B 27/065* (2013.01); *B32B 27/08* (2013.01); *B32B 27/10* (2013.01); *B32B 27/12* (2013.01); *B32B 27/32* (2013.01); *B32B 29/005* (2013.01); *B32B 29/02* (2013.01); *B32B 37/24* (2013.01); *D04H 1/465* (2013.01); *A61F 2013/530562* (2013.01); *A61F 2013/530591* (2013.01); *B05D 2401/32* (2013.01); *B32B 37/0076* (2013.01); *B32B 2255/02* (2013.01); *B32B 2255/10* (2013.01); *B32B 2255/12* (2013.01); *B32B 2262/0253* (2013.01); *B32B 2262/062* (2013.01); *B32B 2307/51* (2013.01); *B32B 2307/546* (2013.01); *B32B 2307/714* (2013.01); *B32B 2307/718* (2013.01); *B32B 2307/726* (2013.01); *B32B 2307/728* (2013.01); *B32B 2307/7265* (2013.01); *B32B 2307/73* (2013.01); *B32B 2307/732* (2013.01); *B32B 2555/02* (2013.01); *Y10T 428/239* (2015.01); *Y10T 428/24893* (2015.01)

(58) Field of Classification Search
CPC .......... A61F 2013/530481; A61F 2013/53051; A61F 2013/530562; A61F 2013/53933; A61F 13/15585; A61F 13/53; A61F 13/5323; A61F 13/539
See application file for complete search history.

(56) References Cited

U.S. PATENT DOCUMENTS

| 5,030,314 | A | 7/1991 | Lang | |
|---|---|---|---|---|
| 5,411,497 | A | 5/1995 | Tanzer | |
| 5,593,399 | A * | 1/1997 | Tanzer | A61F 13/5323 |
| | | | | 604/358 |
| 5,938,650 | A | 8/1999 | Baer | |
| 6,015,608 | A | 1/2000 | Koslow | |
| 8,633,347 | B2 * | 1/2014 | Bianco | A61F 13/5323 |
| | | | | 604/378 |
| 9,295,593 | B2 | 3/2016 | Van Malderen | |
| 2002/0095127 | A1 | 7/2002 | Fish et al. | |
| 2003/0208177 | A1 | 11/2003 | D'Alessio et al. | |
| 2006/0004334 | A1 | 1/2006 | Schlinz | |
| 2007/0088308 | A1 | 4/2007 | Ehmsperger | |
| 2007/0167928 | A1 | 7/2007 | Becker et al. | |
| 2007/0219523 | A1 * | 9/2007 | Bruun | A61F 13/5323 |
| | | | | 604/385.101 |
| 2008/0312618 | A1 | 12/2008 | Hundorf et al. | |
| 2008/0312621 | A1 | 12/2008 | Humdorf et al. | |
| 2009/0112175 | A1 * | 4/2009 | Bissah | A61F 13/4756 |
| | | | | 604/385.101 |
| 2015/0038929 | A1 * | 2/2015 | Van Malderen | A61F 13/515 |
| | | | | 604/385.01 |
| 2015/0148766 | A1 * | 5/2015 | Nakakado | B29C 66/7294 |
| | | | | 604/385.01 |

FOREIGN PATENT DOCUMENTS

| EP | 1632206 | A1 | 8/2006 | |
|---|---|---|---|---|
| EP | 1655007 | A1 | 10/2006 | |
| GB | 2283680 | A | 5/1995 | |
| JP | 2004350864 | A * | 12/2004 | |
| JP | 2006-263074 | A | 10/2006 | |
| WO | 95/21596 | A1 | 8/1995 | |
| WO | WO-2008117109 | A1 * | 10/2008 | ......... A61F 13/5323 |
| WO | WO-2012052172 | A1 * | 4/2012 | ............ A61F 13/15 |

* cited by examiner

ABSORBENT STRUCTURE WITH PERMANENT AND TEMPORARY ATTACHMENTS

CROSS-REFERENCE TO RELATED APPLICATIONS

This application is a continuation of U.S. patent application Ser. No. 13/879,454, filed Apr. 15, 2013, abandoned, which claims priority from PCT/EP2011/003139, filed Oct. 13, 2011 claiming priority from EP10447024.0, filed Oct. 13, 2010, EP10447023.2, filed Oct. 13, 2010, EP10447022.4, filed Oct. 13, 2010, EP10447021.6, filed Oct. 13, 2010, EP10447020.8, filed Oct. 13, 2010 and EP11153268.5 filed Feb. 3, 2011 all of which are incorporated in full in this application as if set forth in its entirety herein.

FIELD OF THE INVENTION

The present invention relates to an absorbent structure having a high concentration of absorbent polymer material within an integrated fluid management system, preferably for use in an absorbent product, such as for example used in the food industry (e.g. coffee pads), the consumer industry (e.g. disposable body warmers), the household industry (e.g. sheet formed detergent articles), building and construction (e.g. filter materials and insulation), beauty and medical industry (e.g. make-up pads, anti-septic wads) and absorbent articles as used in the personal hygiene industry (e.g. feminine hygiene garments, baby diapers and pants, adult incontinence garments). The present invention also relates to an absorbent article comprising such absorbent structure and to a method and apparatus for manufacturing such absorbent structure.

BACKGROUND OF THE INVENTION

Disposable absorbent articles have an absorbent structure for absorbing bodily exudates, a soft liquid-permeable top sheet on the wearer side and a liquid-impermeable back sheet on the garment side. The absorbent structure in between is normally made from a mixture of cellulose fibers or other fibrous substance and an absorbent polymer material. These fibrous substances make these absorbent articles typically quite fluffy and bulky.

In recent years there has been increasing demand for flexible, thinner, lightweight absorbent structures to resolve various problems of manufacturing, marketing, design, fit, wearing comfort, distribution, garbage disposal, material and energy consumption, transportation and storage costs and the like.

The most common method currently used to meet these demands in disposable absorbent articles is to reduce the amount of cellulose fibre or other support material within and surrounding the absorbent structure and/or use larger amounts of absorbent polymer materials. Consequently such absorbent articles have a smaller proportion of hydrophilic cellulose fibres and/or a higher proportion of absorbent polymers materials. Some of these absorbent articles may be better at storing liquid, however they are not necessarily good at absorbing and distributing liquid when the absorbent article is actually being used. It will thus be apparent from the above that the absolute and relative proportions of the fibrous material and absorbent polymer material are closely linked in light of article performance. Hence there are limits on reducing the amount of hydrophilic cellulose fibre and reducing the thickness of absorbent cores.

Many attempts have been undertaken to manufacture flexible, thin, lightweight absorbent structures, consisting of a high amount of absorbent polymer material. In order to obtain good absorbency, distribution and retention within such absorbent structures it has found to be important to at least partially immobilize the absorbent material. Failing to provide sufficient structural integrity results in loss of functional performance characteristics such as coherence, absorption, distribution and/or retention and results in failures related but not limited to for instance leakages, high rewet values, etc. On the other hand however the presence of this physical and/or chemical interaction in between the absorbent material and the restraining material often also leads to a reduced absorption, distribution and/or retention performance. This is especially the case when such flexible, thin, lightweight absorbent structures, consisting of an absorbent polymer material are placed in between multiple enveloping layers.

The larger proportion of absorbent polymer materials and related immobilisation requirements in substantially cellulose free absorbent articles may thus greatly inhibit the absorption, distribution and/or retention of liquids if inadequately managed. It will be clear that the absolute and relative proportions of the hydrophilic cellulose fibres and absorbent polymer materials need to be tightly controlled in order to maintain the absorbent properties of the absorbent structures. Certainly decreased absorption speed and fluid distribution are common causes of failure. Since such hygienic absorbent articles are generally also disposable and need in some instances to be worn over many hours they require performance in a dry state as well as in a partially and fully bodily exudates loaded state.

The ability and capacity of an absorbent polymer material to absorb, distribute and retain liquid is dependent upon the form, position and/or manner in which the absorbent polymer material is incorporated into the absorbent structure. Since many absorbent structures have a relatively homogeneous and continuous distribution of absorbent polymer material, and thus exhibit a substantial homogeneous swelling, for second, third and next liquid insults such absorbent layers may actually act as a liquid barrier. This gel-blocking occurs when the absorbent polymer material located in regions of first contact starts to increase in volume as a consequence of imbibing the fluid, thereby forming a hydrogel. Gel blocking in and adjacent a zone of the absorbent layer of initial liquid contact prevents liquid from rapidly dispersing or wicking past the "blocking" material into the rest of the absorbent layer and further liquid uptake by the absorbent layer must then take place via for instance a diffusion process that is much slower than the rate at which liquid is applied to the absorbent layer. Especially when absorbent polymer material concentrations are absolutely or relatively high and wetted, the hydro-gel can block the initial and/or additional fluid from reaching other still more absorbent regions of the absorbent core, thus leading to unappreciated, underused or unused absorbent capacity. The diminished capacity results in leakages, well before the absorbent core is fully saturated.

Gel-blocking is even increased in thin substantially cellulose free structures where the liquid find little or limited macroscopic voids and/or spaces which can be used for temporary, intermediate or final liquid storage. Also the structural volume restrictions of these absorbent structures lead to a further reduced absorbent performance due to limited swelling capacity of the absorbent polymer material increasing the tendency to functional failures and leakages. To remedy, absorbent article designers have and typically use additional side cuffs and acquisition layers which are expensive, inefficient and can only partly remedy these limitations. By not completely abandoning the use of hydrophilic fibrous materials next to the use of absorbent polymer materials this problem can be partially resolved, however, it will be clear that in such case the absolute and relative proportions of absorbent materials will unwillingly be restricted and thus any thickness reduction of the absorbent structure not fully optimised.

Multiple attempts have been made to provide the above flexible, thinner, light-weight absorbent articles comprising from low cellulose to substantially cellulose to completely cellulose free absorbent structures combining absolute and/or relative high proportions absorbent polymer material versus remaining absorbent materials:

WO95/17868, hereby incorporated by reference, discloses an absorbent structure comprising two fibre layers and an intermediate layer comprising an absorbent polymer material in an amount exceeding 120 g/m$^2$ and particles of a thermoplastic material. While this construction may provide good immobilisation of the absorbent polymer material in the dry state, it seems that only a lesser immobilisation can be achieved in the liquid loaded state. The thermoplastic material appears to stretch to a much lesser extent than the potential swelling of the absorbent polymer materials. Therefore, in particular when the absorbent structure is to be used in an absorbent article to absorb and retain high amounts of bodily exudates, for example a diaper or pants, the absorbent structure disclosed herein may not be fully satisfactory. Furthermore the fibrous bulk material increases thickness and weight, reduces flexibility and raises the cost and environmental footprint of the absorbent structure which is highly unfavourable and undesirable.

WO95/26209, hereby incorporated by reference, describes an absorbent structure having a region containing absorbent polymer material in high homogenous and continuous quantities in the absence of any significant fibrous support material which however typically leads poor fluid management. By poor fluid management it is meant that the regions of absorbent polymer material have insufficient integrity in dry, partially wet and/or wetted state. This results in the physical continuity (and thus the capability of acquiring and transporting fluids through interstitial voids and capillaries) of the hydrogel formed upon swelling in the presence of fluids being substantially disrupted and altered, leading to the hydrogel layers being unintentionally separated, having gaps being introduced, having areas that are significantly thinned and/or broken up into a plurality of underperforming segments. Obviously this minimizing or completely negating coherence, permeability and flow conductivity properties of the absorbent structure results in highly undesirable performance and unacceptable product failure.

EP1447066, hereby incorporated by reference, describes an absorbent structure for the use in an absorbent article which aims to provide an improved immobilization of absorbent polymer material. An absorbent structure is disclosed comprising a non-woven substrate layer, a layer of thermoplastic material in the form of a hot melt adhesive which bonds to the substrate layer to define a thermoplastic immobilizing web which captures the absorbent polymer material. However, in order to adequately secure the absorbent material, one needs to use a significant amount of thermoplastic material, which obviously leads to much higher costs and unappreciated stiffness and rigidity, thereby reducing good product fit, comfort and discreetness. Also, due to its internal cohesion, the layer of thermoplastic material exerts pressure and offers resistance against the free and complete swelling and take-up capacity and thus overall absorption performance of the absorbent material. Furthermore the very high quantities of thermoplastic material lead to physical and chemical shielding of the absorbent polymer materials from the fluids, leading to unavoidable reduced absorption, distribution and retention performance and importantly due to their single use put forward a significant burden on society, industry and families from economic, environmental and sustainability view. Therefore, such absorbent structures are considered to be unfavourable.

Whilst the above attempts describe various approaches to various problems, it is believed that none of these absorbent structures leads to very favourable and performing absorbent structures or articles. The inefficient use of the absorbent material capacity and complex manufacturing processes makes neither of the above absorbent articles economically, technically and/or environmentally advantageous.

Hence, there is still an need in the art for an improved thin, flexible, lightweight absorbent structure with high concentrations of absorbent polymer material which overcomes the problems of the prior art which is discreet, sustainable and/or relatively inexpensive taking in mind manufacturing, marketing, design, fit, comfort, distribution, packaging, disposal, material, energy and transportation costs while preserving the required fluid absorption, distribution, transport, coherence and retention properties. There is furthermore also a need for a method and apparatus to produce such absorbent structures at high production speed and low energy and raw material consumption.

SUMMARY OF THE INVENTION

As a result of exhaustive research to address the above-identified, derived and related problems, the inventor has found that substantially cellulose free absorbent structures continuously immobilising absorbent polymer material via initial smaller pockets (preferably more in amount compared to later compartments) and subsequently larger compartments (preferably less in amount compared to initial pockets) allows excellent fluid management in relation to the available absorbent polymer material in dry, partially and fully liquid loaded state. In a preferred embodiment according to the invention, the absorbent structures according to the present invention allow excellent fluid management of absorbent polymer material by providing a plurality of initial smaller-sized pockets adequately immobilizing dry absorbent polymer clusters thus avoiding unwanted migration and movement thereof in dry state, while during liquid uptake and expansion of the absorbent polymer materials, the absorbent structure swells non-homogenously by gradually unleashing and combining the pockets into fewer and bigger-sized compartments immobilizing the wet absorbent polymer materials thereby avoiding excess restraining or restriction in wet state; thereby advantageously creating an internal fluid management as well as an external liquid management surface structure.

Such absorbent structure volume increases are preferably result of temporary secondary attachment patterns made up for instance from ultrasonic bonds, preferably in combination with the substantially permanent primary attachment grids for instance also made up by ultrasonic bonds, allowing the release of bigger volumes from the initial smaller volumes by detachment of the secondary attachments. In an alternative embodiment however these absorbent structure volume increases are the result of using flexible, extensible, elastic, stretchable and/or elastomeric materials such as for instance elastic non-woven and/or breakable materials such as for instance semi-rigid, rigid and/or stiff paper or tissue respectively allowing additional expansion of and/or breaking up to larger volumes.

In a preferred embodiment the absorbent structure immobilizes, retains and/or restrains the particulate material and the attachments seal, bond and/or join at least part of the outer layers together via ultrasonic bonding, thermo-bonding, pressure-bonding and/or glue-bonding means. These attachments preferably form and/or define pockets which can contain particulate material, whereby the attachment regions comprise essentially and preferably no particulate material. Preferably the absence of an excess or the complete elimination of synthetic immobilisation admixtures (e.g. adhesive and binders, such as thermoplastic glues and webs) used for covering, restraining or bonding absorbent polymers makes the structure technically, environmentally and economically very favourable. In an alternative embodiment however, the composite structure is covered with such thermoplastic materials, glues, binders and/or adhesives to fixate, pocket, encapsulate, bind and/or join these particulate material clusters to and/or in between one or more layers. Additional materials and/or layers to provide extra functional and/or structural advantages such as strength, acquisition, absorption, distribution, transport, retention, etc. may also be incorporated.

In a preferred embodiment a substantially cellulose free absorbent structure is provided comprising a carrier layer, an auxiliary layer and an absorbent polymer material there between, the carrier layer and auxiliary layer being at least partially joined together by attachments made up of substantially permanent primary attachment grids and/or substantially temporary secondary attachment patterns, so as to form a sandwich-like composite structure containing patterned absorbent particulate polymer materials provided in at least some of the unattached regions between the carrier layer and auxiliary layer forming an absorbent polymer material area, the plurality of smaller-sized pockets made up by at least substantially temporary secondary attachments define spaces which immobilize the available dry volume absorbent polymer material, the substantially temporary secondary attachment being gradually releasable as a result of exposing the surrounding absorbent polymer material to liquid so as phase in an intermediate volume increase to fewer and medium-sized compartments immobilising the partially wetted absorbent polymer material, and resulting in still fewer maximum-sized compartments immobilising the wetted absorbent polymer material to obtain continuous fluid management.

In a preferred embodiment a method for the manufacturing of an absorbent structure is provided which comprises: providing a carrier layer, covering the carrier layer with an absorbent material, covering the absorbent material with an auxiliary layer which is joinable to the carrier layer; and in at least one position substantially temporary and/or substantially permanently attaching the auxiliary layer to the carrier layer, and by means of at least substantially temporary secondary attachments defining small-sized pocket wherein dry absorbent material is immobilized, such that by means of gradual release of substantially temporary secondary attachment patterns bigger-sized intermediate and final compartments are provided, thereby continuously immobilising the absorbent material from dry to wetted state.

In a further aspect, the invention provides an absorbent article comprising an absorbent structure as provided by the invention. In another aspect the present invention provides a method and apparatus for the manufacturing of such an absorbent structure.

As also described in EP priority application 10447020.8 and hereby incorporated by reference, an absorbent sandwich-like structure is provided which comprises a distribution layer with an absorbent capacity and an immobilisation layer which joins to the distribution layer to define compartments there between containing intermediate absorbent material. In particular an absorbent structure for use in an absorbent article comprises a distribution layer having an absorbent capacity of at least about 5 $g/m^2$, an immobilisation layer which is joined to the distribution layer to define compartments there between, and an absorbent material held in at least one of the compartments, wherein said absorbent material comprises an absorbent polymer material and from zero to an amount less than about 40 weight percent absorbent fibrous material, based on the weight of absorbent polymer material. The absorbent structure provides in particular an increased fluid communication structure including better adsorption and dispersion in and between the absorbent polymer material pockets, due to the additional wicking and mass flow of liquids caused by the distribution layer, limiting gel blocking, reducing rewet and minimizing leakages. It further provides for a method and apparatus to produce such absorbent structures at high production speed with low energy and raw material consumption.

As also described in EP priority application 10447021.6 and hereby incorporated by reference, an absorbent sandwich-like structure is provided which comprises a substantially liquid-impermeable wicking layer and an immobilisation layer which joins to the wicking layer to define compartments there between containing intermediate absorbent material. In particular an absorbent structure for use in an absorbent article comprises a substantially liquid-impermeable wicking layer, and an immobilisation layer which is joined to the substantially liquid-impermeable wicking layer to define compartments there between, and an absorbent material held in at least one of the compartments, wherein said absorbent material comprises an absorbent polymer material, and from zero to an amount less than about 40 weight percent absorbent fibrous material, based on the weight of absorbent polymer material. The substantially liquid-impermeable wicking layer allows unbound liquids such as water, urine and/or other bodily exudates to more easily spread out, which allows better distribution and transport so as to wet the side and lower sides of the absorbent polymer materials within the pockets. It ensure lower rewet values, less leakage risk and less surface wetness and thus increased reliability of the overall structure. It further provides for a method and apparatus to produce such absorbent structures at high production speed with low energy and raw material consumption.

As also described in EP priority application 10447022.4 and hereby incorporated by reference, an absorbent sandwich-like structure is provided which comprises a carrier layer, an auxiliary layer and an intermediate absorbent particulate material there between wherein substantially primary attachments and substantially secondary attachments join the carrier layer and auxiliary layer together, whereby the secondary attachments are loosened as a result of exposing the absorbent structure to liquid whereas the primary attachments remain substantially intact. It further provides for a method and apparatus to produce such absorbent structures at high production speed with low energy and raw material consumption.

As also described in EP priority application 10447023.2 and hereby incorporated by reference, an absorbent sandwich-like structure is provided which comprises a carrier layer, an auxiliary layer and an intermediate absorbent material there between wherein substantially permanent primary attachments and substantially temporary secondary attachments join the carrier layer and auxiliary layer together, whereby the absorbent structure is made to in-homogeneously swell as a result of exposing the absorbent structure to liquid to form a liquid-managing surface structure. It further provides for a method and apparatus to produce such absorbent structures at high production speed with low energy and raw material consumption.

As also described in EP priority application 10447024.0 and hereby incorporated by reference, a method and apparatus is provided for forming a sandwich-like structure, by depositing particulate material in a desired pattern onto a moving carrier layer. In particular a method for depositing particulate material in a desired pattern onto a moving carrier layer is provided, which provides a clustering means with perforations corresponding to a desired pattern, driving the clustering means in the same direction as and in close proximity to the moving carrier layer, feeding a particle material stream from a particulate material supply means and directing the particle material stream through the clustering means onto the carrier layer. Preferably the particulate materials are clustered via the inlet regions of the perforations and released via the outlet regions of the clustering means. The method allows accurate forming of a predetermined pattern of particulate material clusters at high production speed, with reduced raw material usage and relative low cost. It furthermore provides the improved thin, flexible, lightweight particulate material absorbent structures with discretely deposited particulate material clusters thereon, complemented with an auxiliary layer, such as for instance non-woven, tissue, paper, thermoplastic material and the like and/or affixed by attachment means, such as for instance glue, bonds, joints and the like, with particulate material clusters relatively immobilized there between so as to obtain a sandwich structure usable in the form of an absorbent structure.

As also described in EP priority application 10447027 and hereby incorporated by reference, a method and apparatus is provided for forming a sandwich-like structure, by positioning particulate material in a desired pattern onto a moving carrier layer. In particular a method for positioning particulate material in a desired pattern onto a moving carrier layer is provided, providing a first material, an intermediate material and a second material, whereby prior to joining the first material to the second material, the distribution of the intermediate particulate material is altered through an airflow. In a preferred embodiment the intermediate particulate material is provided substantially homogeneously on the first material prior to applying the positioning airflow. When the intermediate material is undesirable in the attachment area, the method describes the use of airflows, resulting from blowing and/or suction holes to evacuate the intermediate material from the attachment area prior to or during bonding, leading to improved and controllable attachment properties, thus increasing attachment quality and utilisation of energy or materials. It furthermore provides improved thin, flexible, lightweight absorbent particulate structures.

The product, method and apparatus according to preferred embodiments of the invention lead to highly appreciated thin, flexible and/or light-weight absorbent structures which are economically, environmentally, technically and/or commercially advantageous, not in the least since they are obtained without the need for substantial and bulky amounts of fibrous absorbent materials such as fluff and wood pulp (allowing "fluffless" advertisement claims) and are not using substantial and expensive amounts of glue, binder, adhesive and/or other thermoplastic materials (allowing "glueless" advertisement claims). This is unprecedented within the art.

DETAILED DESCRIPTION OF THE INVENTION

Figure 1A:
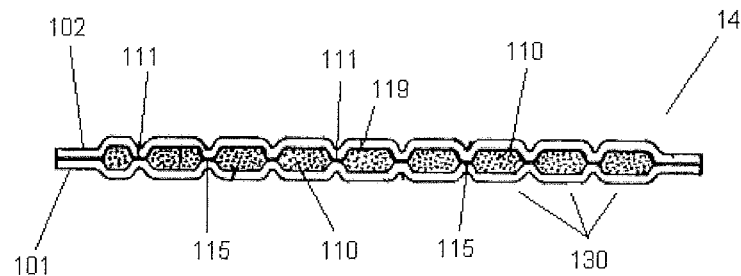
FIG. 1A-D provides cross-sectional schematic illustrations of absorbent structures according to embodiments of the invention.

The present invention relates to an absorbent structure for use in absorbent products, such as coffee pads, disposable body warmers, sheet formed detergent articles, filter material, insulation material, make-up pads, anti-septic wads, and preferably absorbent articles from the personal hygiene industry such as but not limited to feminine hygiene garments, baby diapers and pants, adult incontinence garments, various absorbent holders, liners, towels, inserts and the like; and to a method and manufacturing of the same.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, insofar such variations are appropriate to perform in the disclosed invention. However, it is to be understood that the value to which the modifier "about" refers is itself also specifically disclosed.

"Absorbent article", "absorbent garment", "absorbing article", "absorbing garment", and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent core" as used herein refers to a three-dimensional part of the absorbent structure, comprising liquid-absorbing material, useful to absorb and/or retain bodily exudates.

"Absorbent component" as used herein refers to a structural constituent of an absorbent structure, e.g., a piece of an absorbent core, such as one of multiple pieces in a multi-piece absorbent core.

"Absorbent element" as used herein refers to a part of a functional constituent of an absorbent structure, e.g., a liquid acquisition layer, a liquid distribution layer, or a liquid storage layer formed of a material or materials having particular liquid handling characteristics suitable for the specific function.

"Absorbent insert" as used herein refers to a device adapted for insertion into an absorbent article and to serve as an absorbent structure when so inserted.

"Absorbent layer" as used herein refers to a term referring to a discrete, identifiable sheet-like or web-like element of an absorbent structure which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "superabsorbent polymer", "SAP" and the like as used herein are used interchangeably and refer to any suitable particulate (e.g., flaked, particulate, granular, or powdered) or fibrous cross linked polymeric materials that can absorb at least 5 times and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g bond area's) or unintentional (e.g. manufacturing artefacts).

"Absorbent particulate polymer material" as used herein refers to an absorbent polymer material which is in particulate form such as powders, granules, flakes and the like so as to be flowable in the dry state.

"Absorbent structure" as used herein refers to those elements of an absorbent article comprising material, or a combination of materials suitable to absorb, distribute and retain bodily exudates.

"Absorption" as used herein refers to the process by which a liquid is taken up within a material.

"Acquisition layer", "acquisition region", "acquisition surface" or "acquisition material" and the like as used herein refer to a layer having a faster liquid uptake capability.

"Absorbency" is the ability of a material to take up fluids by various means including capillary, osmotic, solvent, chemical or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibres or particles in an air stream and condensing them from the air stream onto a moving screen by means of a pressure or vacuum; a web of fibres produced by airlaying is herein referred to an "airlaid"; an airlaid web bonded by one or more techniques to provide fabric integrity is herein referred to an "airlaid nonwoven".

"Apparent density" as used herein refers to the basis weight of the sample divided by the calliper with appropriate unit conversions incorporated therein. Apparent density used herein has the unit $g/cm^3$.

"Attach", "attached" and "attachment" as used herein are synonymous with their counterparts of the terms "fasten", "affix", "secure", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to underwear intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, $g/m^2$ or gsm.

"Bodily exudates", "body exudates", "bodily fluids", "body fluids", "bodily discharges", "body discharges", "liquids" and the like as used herein are used interchangeably and refer to, but are not limited to urine, blood, vaginal discharges, breast milk, sweats and faecal matter.

"Binder", "adhesive", "glue", "resins", "plastics" and the like as used herein are used interchangeably and refer to substances, generally in a solid form (e.g. powder, film, fibre) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded.

"Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination.

"Cellulose fibres" as used herein refers to naturally occurring fibres based on cellulose, such as, for example cotton, linen, etc.; wood pulp fibres are one example of cellulose fibres; man-made fibres derived from cellulose, such as regenerated cellulose (rayon), or partially or fully acetylated cellulose derivatives (e.g. cellulose acetate or triacetate) are also considered as cellulose fibres.

"Cluster" or the like as used herein refers to an agglomeration of particles and/or fibres.

"Chemically stiffened fibres", chemically modified fibres", "chemically cross-linked fibres", "curly fibres" and the like as used herein are used interchangeably and refer to any fibres which have been stiffened by chemical means to increase stiffness of the fibres under both dry and aqueous conditions, for example by way of addition of chemical stiffening agents (e.g. by coating, impregnating, etc.), altering the chemical structure of the fibres themselves (e.g. by cross-linking chains, etc.) and the like.

"Cohesion" as used herein refers to the resistance of similar materials to be separated from each other.

"Comprise," "comprising," and "comprises" and "comprised of" as used herein are synonymous with "include", "including", "includes" or "contain", "containing", "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight nonwoven material used to contain and conceal an underlying absorbent core material; examples are the facing layer or materials that cover the absorbent cores of feminine hygiene garments, baby diapers and pants and adult incontinence garments.

"Crotch region" of an absorbent article as used herein refers to about 50% of the absorbent article's total length (i.e., in the y-dimension), where the crotch point is located in the longitudinal centre of the crotch region. That is, the crotch region is determined by first locating the crotch point of the absorbent article, and then measuring forward and backward distance of 25% of absorbent article's total length.

"Cross direction (CD)", "lateral" or "transverse" and the like as used herein are used interchangeably and refer to a direction which is orthogonal to the longitudinal direction and includes directions within ±45° of the transversal direction.

"Curing" as used herein refers to a process by which resins, binders or plastics are set into or onto fabrics, usually by heating, to cause them to stay in place; the setting may occur by removing solvent or by cross-linking so as to make them insoluble.

"Diaper", "conventional diaper", "diaper-like", "diaper-like garment" and the like as used herein are used interchangeably and refer to disposable absorbent articles, which typically include a front waist portion and a back waist portion which may be releasably connected about the hips of the wearer during use by conventional fasteners such as adhesive tape fasteners or hook and loop type fasteners. In use, the article is positioned between the legs of the wearer and the fasteners are releasably attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Distribution layer", "distribution region", "distribution surface" or "distribution material" and the like as used herein are used interchangeably and refer to a layer having a larger capacity in wicking, dispersing and distributing liquids.

"Drylaying" as used herein refers to a process for making a nonwoven web from dry fibre; these terms apply to the formation of carded webs, as well as to the air laying formation of random webs; a web of fibres produced by drylaying is herein referred to as a "drylaid"; a drylaid web bonded by one or more techniques to provide fabric integrity is herein referred to a "drylaid nonwoven".

"Dry strength" as used herein refers to the strength of an adhesive attachment determined in dry state conditions, immediately after drying under specified conditions or after a period of conditioning in the standard laboratory atmosphere.

"Fabric" as used herein refers to a sheet structure made from fibres, filaments and/or yarns.

"Feminine hygiene garments" as used herein refer to absorbent hygiene articles intended to be worn by woman, for absorbing and containing body exudates.

"Fibre" as used herein refers to the basic threadlike structure from which nonwovens, yarns and textiles are made. It differs from a particle by having a length at least 4 times its width; "Natural fibres" are either of animal (wool, silk), vegetable (cotton, flax, jute) or mineral (asbestos) origin, while "Man-made fibres" may be either polymers synthesised from chemical compounds (polyester, polypropylene, nylon, acrylic etc.) or modified natural polymers (rayon, acetate) or mineral (glass). "Fibre" and "filament" are used interchangeably.

"Film", "foil" and the like as used herein are used interchangeably and refer to a thin sheet of essentially non-absorbent material such as plastic or closed foams. In this invention it particularly refers to materials that do not correspond to non-wovens.

"Fluff pulp" as used herein refers to wood pulp specially prepared to be drylaid.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the back sheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"Highloft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilisation layer" as used herein refers to a layer able to be applied to the absorbent polymer material or absorbent polymer material area with the intent to compartmentalize, bond and/or immobilize absorbent material and/or layer.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibres with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered." "Upper" refers to the layer of the absorbent article which is nearest to and faces the wearer facing layer; conversely, the term "lower" refers to the layer of the absorbent article which is nearest to and faces the garment facing layer. "Layer" is three dimensional structure with a x dimension width, y dimension length, and z-dimensions thickness or calliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (MD)", "longitudinal" and the like as used herein are used interchangeably and refer to a direction running parallel to the maximum linear dimension of the structure and includes directions within ±45° of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the flow of a liquid from one absorbent element or component to another absorbent element or component by channel flow action.

"Mechanical bonding" as used herein refers to a method of bonding fibres by entangling them. This can be achieved by needling, stitching with fibres or by the use of high-pressure air or water jets and the like.

"Non-woven" as used herein refers to manufactured sheet, web or batt of directionally or randomly orientated fibres, bonded by friction, and/or cohesion and/or adhesion, excluding paper and products which are woven, knitted, tufted, stitch-bonded incorporating binding yarns or filaments, or felted by wet-milling, whether or not additionally needled. The fibres may be of natural or man-made origin and may be staple or continuous filaments or be formed in situ. Commercially available fibres have diameters ranging from less than about 0.001 mm to more than about 0.2 mm and they come in several different forms: short fibres (known as staple, or chopped), continuous single fibres (filaments or monofilaments), untwisted bundles of continuous filaments (tow), and twisted bundles of continuous filaments (yarn). Nonwoven fabrics can be formed by many processes such as melt blowing, spun bonding, solvent spinning, electro-spinning, and carding. The basis weight of nonwoven fabrics is usually expressed in grams per square meter (gsm).

"Pant", "training pant", "closed diapers", "pre-fastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Resin" as used herein refers to a solid or semisolid polymeric material.

"Substantially cellulose free" as used herein refers to an absorbent article, structure or core, that contains less than 40% by weight cellulosic fibres, less than 20% cellulosic fibres, less than 5% cellulosic fibres, no cellulosic fibres, or no more than an immaterial amount of cellulosic fibres which do not materially affect the thinness, flexibility or absorbency thereof. This also encompasses completely cellulose free.

"Thermobonding" as used herein refers to a method of bonding fibres by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localised heat through vibration thereby causing fibres to bond to one another.

"Water-absorbing", "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of interlacing two or more sets of yarns at right angles to form a fabric; a web of fibres produced by weaving is herein referred to as a "Woven".

"Web material" as used herein refers to an essentially endless material in one direction, i.e. the longitudinal extension or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (the y-direction) will be significantly larger than the thickness, but less than the length. Often, though not necessarily, the thickness and the width of such materials is essentially constant along the length of the web. Without intending any limitation, such web materials may be cellulosic fibre materials, tissues, woven or non-woven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, nonwoven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of an adhesive attachment determined immediately after removal from a liquid in which it has been immersed under specified conditions of time, temperature and pressure. The term is commonly used in the art to designate strength after immersion in water.

"Wetlaying" as used herein refers to the forming a web from an aqueous dispersion of fibres by applying modified paper making techniques; a web of fibres produced by wetlaying is herein referred to as a "wetlaid".

"Wood pulp" as used herein refers to cellulosic fibres used to make viscose rayon, paper and the absorbent cores of products such as feminine hygiene garments, baby diapers and pants and adult incontinence garments.

"X-y dimension" as used herein refers to the plane orthogonal to the thickness of the article, structure or element. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

The recitation of numerical ranges by endpoints includes all numbers and fractions subsumed within that range, as well as the recited endpoints.

The absorbent structure according to the invention, preferably a substantially cellulose free structure, comprises a carrier layer, an auxiliary layer and an absorbent material provided between said carrier layer and said auxiliary layer to form a sandwich wherein initial smaller pockets (preferably more in relative amount as compared to later compartments) and subsequently larger compartments (preferably less in relative amount as compared to initial pockets) allows excellent fluid management of the absorbent polymer material in dry, partially and fully liquid loaded state. The absorbent structures according to the present invention allow sufficient internal immobilization of the absorbent polymer material in dry state by providing well-designable customized smaller pockets containing the unexpanded dry materials and subsequently by providing well-designable customised bigger compartments containing the wetted materials, while avoiding restraining or restriction of the swelling and volume-expanding absorbent material in wetted state, thereby preventing underutilisation, loss or negative impact on their absolute and relative performance, giving rise to superficial liquid management surfaces.

In a preferred embodiment according to the invention the fluid and liquid management absorbent structure contains a pre-defined pattern of secondary attachments at least partially joining said enveloping layers together characterized in that the secondary attachments are loosened, dissolved, weakened and/or broken up as a result of exposing said absorbent structure to liquid, vapour and/or moisture. It should be noted that the secondary attachment can but do not have to be water-sensitive, in other words they can thus also be water-insensitive or wet-resistant, as the secondary attachments should preferably be allowed to detach by bringing the absorbent structure in contact with liquid, thus not necessarily the secondary attachments themselves have to be wetted before the absorbent structures displays its fluid and liquid management. Next to more accurate prediction and development of customised release times of the secondary attachments, this is also advantageous since developing and controlling water-sensitive secondary attachments bring much more complexity to the manufacturing process of the absorbent structures leading to slower production speeds, additional energy and material consumption, gives rise to higher prevalence of dysfunctional and non-performing secondary attachment thus to be disposed failing absorbent structures. The mere forces exerted by the swelling absorbent material should thus preferably be sufficient to detach the secondary attachments, independent of them being dry, partially wetted or fully wetted. Preferably the smaller-sized pockets in dry state release under the influence of bringing the absorbent structure into contact with water, thereby forming intermediate-sized compartment made up by the release expanded smaller-sized pockets and/or by the combination of multiple smaller-sized pockets. Preferably these intermediate-sized pockets are formed when the absorbent structure is partially loaded. Even more preferably the medium-sized compartments from partially wetted state enlarge even further under the influence of bringing the absorbent structure into contact with water or upon additional swelling of the absorbent polymer material, thereby forming maximum-sized compartments made up by the release expanded smaller-sized pockets and by the combination of multiple smaller-sized pockets and medium sized compartments. Preferably these maximum-sized pockets are formed when the absorbent structure is almost fully wetted. This controlled and continuous expansion during the wetting process results in unseen fluid management qualities and moreover allows for liquid management superficial structures. This is unseen in the prior art and is highly desirable. Preferably also a pre-defined grid of primary attachments is present throughout the majority of the surface area of the absorbent structure which remain substantially intact under normal usage conditions. The primary attachment can serve the overall structural and functional integrity of the absorbent structure, increase the fluid management systems and/or help with the creation of in-homogenous liquid management surface structure of the absorbent structure. Absorbent structures according to a preferred embodiment of the invention contain absorbent polymer material, more preferably absorbent particulate polymer material such as highly permeable SAP.

In a preferred embodiment according to the invention a single absorbent layer substantially cellulose free absorbent structure for use in an absorbent article is measuring about 10 cm in width by about 40 cm in length, having an average dry thickness from about 0.1 to about 10 mm, more preferably from about 0.5 to about 5 mm, most preferably from about 1-3 mm would contain about 5-25 grams absorbent polymer material, more preferably about 10-20 grams, more preferably 11-15 gram, most preferably about 12-14 grams which would initially be pocketed in about 50-800 small pockets, more preferably about 100-700 pockets, more preferably about 200-600 pockets, more preferably about 300-500 pockets, more preferably about 350-450 pockets and most preferably around 1 pocket per $cm^2$ absorbent structure surface, which would subsequently be gradually released to ultimately form about 1-50 compartments, more preferably about 3-30 compartments, more preferably about 5-25 compartments, more preferably about 10-20 compartment and most preferably about 1 compartment per 15 $cm^2$ absorbent structure surface. Pockets are preferably identical and square-, round- or honeycomb shaped and uniformly and homogenously distributed across the absorbent structure, the compartments are preferably longitudinally distributed and rectangle- or ellipsoid-like shaped having adequate perimeter sealing at the absorbent article edges to avoid liquid management structures guiding and channelling the liquid to edges of the absorbent structure, where certainly the edges of the crotch regions have to be avoided. In essence the shape of the smaller pockets try to accommodate the maximum amount of absorbent polymer on the available surface area, while the bigger compartments try to accommodate the maximum expansion volume of the wetted absorbent polymer materials while ensuring internal fluid management and external liquid management via surface structures. The absorbent polymer material will furthermore preferably be profiled throughout the surface in these dry pockets, hence the need for primary attachment grid and secondary attachment patterns having well-defined and accurate bonding strength to accommodate fluid management and liquid management surface structures according to the invention. The absorbent structure will preferably be complemented by about 30-70 gsm, more preferably about 40-60 gsm and most preferably about 50 gsm highloft acquisition layer and/or similar amounts of curly fibers as distribution layer to allow fast uptake and distribution within the absorbent article, subsequently being enveloped in a liquid permeable topsheet and liquid impermeable breathable backsheet to allow implementation within an absorbent article such as baby diaper or pants.

While preferably such absorbent structure volume increases are result of temporary secondary attachment patterns made up for instance from ultrasonic bonds, preferably the absorbent structures are designed in combination with substantially permanent primary attachment grids for instance also made up by ultrasonic bonds, allowing the release of bigger volumes from the initial smaller volumes by detachment of the secondary attachments, while keeping absorbent polymer integrity and coherence in light of excellent fluid management via the primary attachment pattern safeguarding structural and functional integrity. In an alternative embodiment however these absorbent structure volume increases are the result of using flexible, extensible, elastic, stretchable and/or elastomeric materials such as for instance elastic non-woven and/or breakable material such as for instance semi-rigid, rigid and/or stiff paper or tissue respectively allowing additional expansion from and/or breaking up from smaller to larger volumes.

In certain embodiments according to the present invention all or some of the secondary attachments may for instance be maintained during partial loading of the absorbent structure, while they will only become detached in fully bodily exudates loaded state. In this way initial contact is maintained until swelling forces of the absorbent structure take the upper hand. This de-bonding does preferably not influence the primary attachments, thereby still ensuring functional and/or structural integrity of the absorbent structure and absorbent polymer material area, while however not restraining the swelling of the absorbent polymer material so as to decrease liquid absorption and retention capacity. By preferably not relying on wet-soluble, wet-sensitive or not-wet-resistant secondary attachments the detachment process of the secondary attachment patterns according to the invention can be better controlled and predicted, since such absorbent structures and secondary attachment patterns in use, such as for instance used in absorbent articles such as a baby diaper or pants, will not be prematurely released due to the mere wetting of the (wet-sensitive) attachment means but will only be released when the to be expected and required forces deriving from movement, article strain and absorbent polymer material swelling have been reached. This is especially advantageous in substantially cellulose free absorbent articles as they specifically have to avoid free migration and movement of dry or partially dry absorbent polymer materials in light of lumping, gel blocking and overall absorbent material performance.

In a preferred embodiment the absorbent structure immobilizes, retains and/or restrains the particulate material and the attachments seal, bond and/or join at least part of the pockets and/or outer layers together via ultrasonic bonding, thermo-bonding, pressure-bonding and/or glue-bonding means. These attachments preferably form and/or define pockets which can contain particulate material, whereby the attachment regions comprise essentially and preferably no particulate material. Preferably these attachments are made up from discrete shape rather than substantially continuous lines so as to better control the bonding and debonding process in line with specified bonding strengths for those primary attachments grids and secondary attachment patterns within that absorbent structure according to that embodiment of the present invention. The use well-design dots for instance can be located, shaped and sized in such a manner so as to gradually release the secondary attachment pattern while steadily preserving the primary attachment patterns during any given absorbent structure embodiment. Preferably this is done by the very accurate ultrasonic bonding as opposed to the thermo-mechanical calendaring for instance which are very difficult to control in light of their generated attachment tenacity. Also such calendar systems are caused to be performing very poorly in case any absorbent material is trapped in between the attachments. The absorbent structure according to the present invention overcome these problems. Preferably the absence of an excess or the complete elimination of synthetic immobilisation admixtures (e.g. adhesive and binders, such as thermoplastic glues and webs) used for covering, restraining or bonding absorbent polymer materials makes the structure technically, environmentally and economically very favourable. In an alternative embodiment, the composite structure is covered with such thermoplastic materials, glues, binders and/or adhesives to fixate, pocket, encapsulate, bind and/or join these particulate material clusters to and/or in between one or more layers. Additional materials and/or layers to provide extra functional and/or structural advantages such as strength, acquisition, absorption, distribution, transport, retention, etc. may also be incorporated.

The absorbent structure, preferably substantially cellulose free, according to the invention has several embodiments and preferred embodiments for use in absorbent products such as for instance:

An absorbent structure comprising:
a) a carrier layer; and
b) an auxiliary layer; and
c) an absorbent material provided between said carrier layer and said auxiliary layer wherein pockets release extra volume as a result of exposing said absorbent structure to liquid.

An absorbent structure comprising:
a) a carrier layer; and
b) an auxiliary layer; and
c) an absorbent material provided between said carrier layer and said auxiliary layer wherein relative smaller sized pockets release extra volume so as to form relative bigger sized compartments as a result of exposing said absorbent structure to liquid.

An absorbent structure comprising:
a) a carrier layer; and
b) an auxiliary layer; and
c) an absorbent material provided between said carrier layer and said auxiliary layer wherein a plurality of smaller sized pockets release extra volume so as to form relative fewer bigger sized compartments as a result of exposing said absorbent structure to liquid.

An absorbent structure for use in an absorbent article comprising:
a) a carrier layer; and
b) an auxiliary layer; and
c) an absorbent material provided between said carrier layer and said auxiliary layer wherein a plurality of smaller sized pockets release extra volume so as to form relative fewer bigger sized compartments as a result of exposing said absorbent structure to liquid wherein at least some secondary attachments form pockets characterized in that when the secondary attachments are loosened as a result of exposing said absorbent structure to liquid they form compartments.

An absorbent structure for use in an absorbent article comprising:
a) a carrier layer; and
b) an auxiliary layer; and
c) an absorbent material provided between said carrier layer and said auxiliary layer wherein a plurality of smaller sized pockets release extra volume so as to form relative fewer bigger sized compartments as a result of exposing said absorbent structure to liquid wherein at least some secondary attachments join said carrier layer and said auxiliary layer together to form pockets characterized in that when the secondary attachments are loosened as a result of exposing said absorbent structure to liquid they form compartments.

An absorbent structure for use in an absorbent article comprising:
a) a carrier layer; and
b) an auxiliary layer; and
c) an absorbent material provided between said carrier layer and said auxiliary layer wherein a plurality of smaller sized pockets release extra volume so as to form relative fewer bigger sized compartments as a result of exposing said absorbent structure to liquid wherein at least some primary and secondary attachments join said carrier layer and said auxiliary layer together to form pockets characterized in that when the secondary attachments are loosened as a result of exposing said absorbent structure to liquid they form compartments, whereas the primary attachments remain substantially intact.

An absorbent structure for use in an absorbent article comprising:
a) a carrier layer; and
b) an auxiliary layer; and
c) an absorbent material provided between said carrier layer and said auxiliary layer wherein a plurality of smaller sized pockets release extra volume so as to form relative fewer bigger sized compartments as a result of exposing said absorbent structure to liquid wherein at least some primary and/or secondary attachments join said carrier layer and said auxiliary layer together to form pockets characterized in that when the secondary attachments are loosened as a result of exposing said absorbent structure to liquid the absorbent structure swells in-homogenously so as to form liquid management surface structure.

In a preferred embodiment the following is provided: A substantially cellulose free absorbent structure comprising a carrier layer, an auxiliary layer and an absorbent particulate polymer material there between, the carrier layer and auxiliary layer being at least partially joined together by attachment regions made up of substantially permanent primary attachment grids having relative higher bonding strength and/or substantially temporary secondary attachment patterns having relative lower bonding strength, so as to form a sandwich-like composite structure containing clustered absorbent particulate polymer materials provided in at least some of the unattached regions between the carrier layer and auxiliary layer thereby forming an absorbent polymer material area, the plurality of smaller-sized pockets of substantially equal thickness made up by at least substantially temporary secondary attachments define spaces which immobilize the available dry volume absorbent polymer material, the substantially temporary secondary attachment being gradually releasable as a result of exposing the peripheral absorbent polymer material to liquid so as phase in an intermediate volume increase to fewer medium-sized compartments immobilising the partially wetted absorbent polymer material, subsequently resulting in still fewer maximum-sized compartments immobilising the wetted absorbent polymer material. Preferably it shows non-homogenous swelling due to non-homogeneous swelling of the absorbent polymer materials and/or releasing of the secondary attachments so as to from liquid management structures.

Prior art absorbent structures swell substantially homogeneous and continuous until the available liquid uptake capacity of the absorbent material is reached and/or the available free volume and space within the various absorbent structure boundaries is taken up by the swollen and volume-expanded absorbent materials. The placing of too much absorbent polymer material in smaller and confined pockets which do not have the volume expanding capacities according to the present invention thus lead to underused absorbent material capacities, while the overfilled pockets often result in undesirable lumpy pocket feelings for the handler and user and in extreme cases may cause the pockets to unintentionally rupture thereby expelling the swollen absorbent materials into contact with the user which is to be avoided.

Other absorbent structures foresee in dry state the necessary swelling volume for their subsequent wetted and swollen absorbent polymer material by providing larger and spacious pockets prior to use. However, especially in substantially cellulose free absorbent structure, the required volume leads to the absorbent material not being sufficiently immobilized resulting in free migration, moving and clustering together leading to extremely poor fluid and liquid management. Furthermore the clustering together of absorbent material in too large pockets in dry state causes severe gel-blocking when wetted and more over decreases the overall fit, comfort and discreetness due to the fact these large pockets cause the absorbent polymer material to form significant volumes in parts of the large pockets during usage which are felt by the user in use, which is highly undesirable. The apparent gel-blocking leads to very poor usage of the expensive absorbent polymer materials.

Nevertheless it has been found when absorbent polymer material absorbs liquid and swells it actually performs much more rapidly, effectively and efficiently when it has been disposed in pockets or arrangements. These predefined locations together with the meticulous dosing of absorbent polymer material can thus help to obtain optimal absorbency, fit and/or comfort. It is desirable for absorbent polymer material to remain in its intended location, while unwanted migration and uncontrolled movement thereof within the absorbent structure should be avoided. However the absorbent material is very desirably also immobilized and/or restrained via an absorbent structure in such a way that the absorbent particulate polymer material performs both in partially liquid loaded as well as in fully liquid loaded condition taking in mind required volume expansion for material and structural performance.

The absorbent structure according to present invention is therefore distinguished by its capability to firmly pocket, immobilize and/or restrain absorbent material within the dry state while allowing additional, predetermined, phased and controlled expansion from a multitude of smaller-sized pockets to fewer but bigger-sized unleashed compartments during the wetting of the absorbent structure, thus creating additional (yet unavailable) space, volume and surface area in light of optimal expansion, swelling and/or loading of the absorbent material. While the substantially permanent primary attachment grids will essentially help to safeguard the structural integrity of the absorbent structure since they are substantially resistant to the forces exerted upon them during the wetting and using of the absorbent article, the substantially temporary secondary attachment patterns will allow the rise of unprecedented functionalities, while nevertheless securely encapsulating the absorbent material during gradual phased expansion and swelling.

The absorbent structure attachment grid and pattern is preferably in line with the to be exerted forces generated by the user and by the available and usable absorbent material when being loaded from substantially dry to a partially loaded up to fully liquid loaded state. The primary attachments in essence retain more integrity during and after absorbent structure absorption than the secondary attachments. The difference in bonding strength between the primary attachments and the secondary attachments allows the carrier layer and auxiliary layer to separate between the multiple primary attachment regions, respectively at the secondary attachment regions, thus releasing additional space and volume to allow further and free expansion of the absorbent material in the partially or fully liquid loaded state as opposed to the dry state. This release is brought in line with the volume swelling.

The unlocking of the extra volumes and space during usage only, leads to several manufacturing, storage and transport advantages, since the absorbent materials can now be positioned, clustered and immobilized more accurately and effectively, as the removal of initial restraining means during use allows for deferred fluid and liquid management systems leading to excellent performance and significant raw material savings. Better and controlled liquid wicking and dispersion thus leads to improved fluid communication from less absorbent (e.g. saturated) to the more absorbent area's (e.g. unsaturated).

For reasons of further improved absorbency, fluid distribution, transport, retention and lower amount of leakages and rewet-values, it is preferably desirable for these absorbent structures to have outspoken macroscopic liquid management surface structures such as heights and elevations and/or depressions and valleys which can act as channels, canals and/or embankments to guide the liquid in a desired manner. The absorbent structure comprises a carrier layer, an auxiliary layer and an absorbent material sandwiched there between wherein primary attachments and secondary attachments bond said carrier layer and said auxiliary layer together characterized in that the absorbent structure non-homogeneously swells to form a superficial liquid-managing surface structure as a result of exposing the absorbent structure to liquid.

For reasons of optimal flexibility, fit, comfort, discreetness, transportation and storage efficiency, it is desirable for such three-dimensional macroscopic surface structures to appear and function only when needed, i.e. when the product is partially and/or fully wetted by liquid, and are thus preferably not yet present prior to the usage of the absorbent structure. The invention allows for indirect functionalities, whereby 'hidden' features in dry state are essentially 'unleashed' by wetting, thereby 'revealing' essentially the three-dimensional structures with high(er) elevated and/or low(er) depressed functional and structural parts of the absorbent structure. The three-dimensional swelling of the absorbent structure can be caused by differential swelling of the absorbent polymer material or by the differential grid and pattern of bonding and debonding attachments, or by a combination thereof. In a preferred embodiment, the absorbent structure comprises absorbent materials different in volume absorption capacity, by at least 25%, preferably at least 50%, most preferably at least 100%. By way of example an originally flat cuff being for instance attached between two areas of high absorption would be freed and erect itself when these areas take up liquid and swell.

The inventor has found that the ability to create macroscopic surface structures with internal, incorporated and superficial liquid management systems allow unseen fluid management by enabling liquid guidance towards desired locations with additional uptake, distribution, transport and containment opportunities as effect and thus ensuring a significant increase in efficiency and effectiveness of raw material usage while limiting gel blocking, reducing rewet, minimizes leakage and failure. Preferably the liquid is guided towards the entire surface of the absorbent structure with the exception of the side edges to minimize leakages and product failures.

Ideally the liquid taken up by the absorbent structure and the swelling and volume increase resulting therefrom is in line with the respective spaces and volumes created by the incremental debonding and loosing process of the attachment patterns. While the dry immobilisation of the lower volume absorbent material is secured in the small(ler) pockets formed by the combination of the primary and secondary attachments, the wet immobilisation of the wetted higher volume absorbent material is continuously ensured by the expanding big(ger) compartments defined by intact primary attachments after partial or full release of the secondary attachment patterns under the influence of liquid, vapour and/or moisture. As the absorbent material gains significant volume it is thus important to restrain the absorbent material continuously. Well-designed phased absorbent structures allow gradual expansion of the absorbent material without too little or too excessive restraining and too late or too early detachment of the secondary attachments during the gradual wetting and swelling process. The bonding strength should suffice the parameters of the absorbent structure and will depend on the article, its product size and shape and the required duration of the usage and performance.

It is noted that when stated primary attachments remain substantially intact under influence of liquid, reference is preferably being made to characteristics under relatively normal wearing/usage conditions, typical usage timing, average liquid amounts and intervals at room or body temperatures without taking into account exaggerated, severe and/or extreme conditions such as for example abnormal large amounts of litres of liquid during multiple days of intense contact. In such case, although not preferred, the initially wet-resistant primary attachments might become loosened, detached or broken up after all. It would be clear from the above that such primary attachments eventually turning into secondary attachments after being exposed to prolonged and/or more intense usage conditions than normal are also envisaged under this invention.

Unlike previously existing absorbent articles and methods from the prior art limited by permanent or fully releasable immobilization and/or restraining means leading to unsatisfactory absorbency, distribution and retention parameters combined with limited flexibility, fit and wearing comfort, the present invention overcomes various problems relating thereto and deriving therefrom by having absorbent material containing pockets and compartments with pre-defined and well-managed permanent grids and temporary patterns leading to gradual volume expansion. The present invention furthermore overcomes various problems by having wetted absorbent material forming obstacles and liquid guides thereby providing physical and chemical barriers and blockages preventing leakage and/or providing extra fluid distribution and transport. More specifically the invention allows increased absorbent material expansion and swelling within the unleashed compartments, while additional distribution and transport arises within and in between the absorbent polymer material clusters which have until now been underused and unappreciated.

The present invention thereby does not only provide for an efficacious compartmentalization and restraining of absorbent materials in dry, partially and fully liquid loaded stated, it also allows a significant increase in efficiency and effectiveness of raw materials available in the absorbent structure within partially and fully liquid load state, increases overall absorbency and retention capacities and limits gel blocking, reduces rewet and minimizes leakage.

In a second aspect, the present invention provides an absorbent article comprising, at least in the front half of the absorbent article, an absorbent structure according to an embodiment of the invention. In a preferred embodiment, the absorbent article comprises an absorbent structure comprising a carrier layer and auxiliary layer, whereby the upper surface of the carrier layer is facing the wearer's skin and a lower surface of the auxiliary layer is facing the garment of the wearer. The absorbent material is preferably in direct contact with the lower surface of the auxiliary layer and the upper surface of the carrier layer, however additional fabric, non-woven, woven, tissue and/or paper layer can be provided to accommodate further fluid management and integrity.

It is known that for most absorbent articles, for instance for articles such as feminine hygiene garments, baby diapers, baby pants and adult incontinence products, that liquid discharge occurs predominantly in the front half. It is therefore advantageous to provide an improved absorbent article with an absorbent structure according to an embodiment of the invention in that area where fluid loading and uptake requirement is highest. Obviously, an absorbent article comprising an absorbent structure according to an embodiment of the invention which is entirely or partially located in either the front, crotch and/or back region of the absorbent article, such as for instance a baby diaper, is also covered under this invention. Any combinations thereof are hereby also encompassed.

In the hygiene industry, absorbent articles are specifically designed to absorb, distribute and retain bodily exudates. Apart from taking up liquid and retaining it within the absorbent structure of the absorbent article, the absorbent articles are also intended to satisfactory prevent bodily exudates from soiling, wetting, or otherwise contaminating clothing or other articles, such as bedding, that may possibly or come in contact with the wearer. A disposable absorbent article, such as a disposable diaper, may be worn for several hours in a dry state and/or in liquid loaded state. Accordingly multiple attempts have been made toward improving the fit and wearing comfort of the absorbent article, both when the article is dry and when the absorbent article is fully or partially loaded with bodily exudates, while enhancing the absorption, distribution and retention functions of the absorbent article. Flexible, thin, light-weight and discreet absorbent articles are also here greatly preferred.

A typical absorbent article has a crotch width of about 100 mm and an average core length of about 500 mm. An absorbent article with a crotch width of this dimension provides improved consumer comfort. An absorbent structure according to the present invention achieves a crotch width of preferably less than 85 mm, 80 mm, 75 mm, 70 mm, 65 mm, 60 mm, 55 mm or 50 mm and a core length of preferably less than 500 mm, 450 mm, 400 mm, 350 mm or 300 mm. Hence, preferably an absorbent structure according to the present invention has a crotch width and a core length in line with the above dimensions.

In a third aspect, a method and apparatus to produce an absorbent structure according to an embodiment of the invention used as absorbent core in a feminine hygiene garment, baby diaper, baby pants or adult incontinence garment product. While particular embodiments of the present invention are illustrated and described, it would be obvious those skilled in the art that various other changes and modifications can be made without departing from the spirit and scope of the invention.

Method and apparatus for the manufacturing of an absorbent structure for use in an absorbent article comprising the steps of:
providing a carrier layer;
covering the carrier layer with an absorbent material wherein said absorbent material comprises
i) an absorbent polymer material, and
ii) from zero to an amount less than about 40 weight percent absorbent fibrous material, based on the weight of absorbent polymer material;
covering the absorbent material with an auxiliary layer which is joinable to the carrier layer; and
joining the auxiliary layer to the carrier layer thereby forming primary attachments and secondary attachments that define pockets there between wherein the absorbent material is held in at least one of the pockets, characterized in that, the secondary attachments are loosened, preferably to form larger compartments, as a result of exposing the absorbent structure to a liquid whereas the primary attachments remain substantially intact.

Examples are used below for further non-limitative illustration of the invention.

With reference to FIGS. 1A-D, 2 and 3, the absorbent structure 14 includes at least one carrier layer 101 and at least one auxiliary layer 102, and absorbent material 110. The carrier layer 101 and auxiliary layer 102 are joined via secondary attachments 115, optionally via a secondary attachment media such a for instance glue or hot-melt, and preferably also joined together via primary attachments 111, optionally via primary attachment media such as for instance an adhesive or binder.

It should be noted although absorbent structures using secondary attachments 115 as well as primary attachments 111 are very much preferred, absorbent structures 14 only using secondary attachments 115 without the use of primary attachments 111 are also covered by this invention. One might for instance think about a combination of several pieces of absorbent segments combined to form an absorbent structure 14 which is only using secondary attachments 115 within the absorbent segments so upon wetting to come from a multitude of dry segments with smaller pockets 130 to a multitude of wetted segments with larger compartments. Various combinations, shapes and sizes are of course possible and are hereby encompassed by the present invention.

Figure 1B:
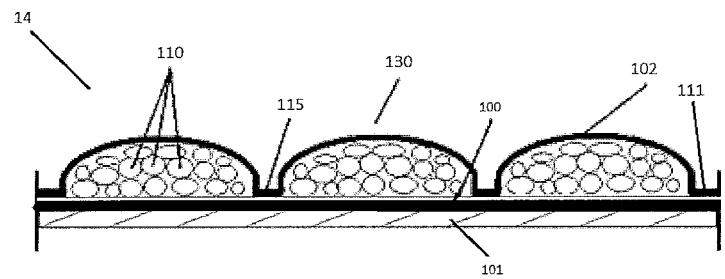

Referring to FIG. 1B, a carrier layer 101 and an auxiliary layer 102 is provided. The carrier layer 101 is covered on one side by discrete amounts of absorbent material 110. The absorbent material 110 is covered by an auxiliary layer 102. The auxiliary layer 102 lies on top of the absorbent material 110 and is joined at regular intervals a distribution layer 100a or wicking layer 100b thereby providing pockets 130 holding the absorbent material 110. The absorbent material 110 preferably comprises absorbent particulate polymer particles, but in addition absorbent fibrous materials can be used. Preferably the amount of absorbent fibrous material used is less than 10 weight percent based on the total weight of absorbent polymer material.

Figure 1C:
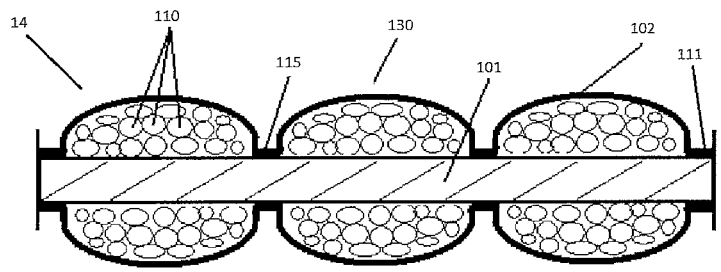

Referring to FIG. 1C, it has been found that absorbent structures 14 can be formed by combining two layers of absorbent material 110. The absorbent structure 14 as shown comprises one carrier layer 101, two layers of absorbent material 110 and two auxiliary layers 102. When two discontinuous layers of an absorbent material 110 are used, being one on the wearer facing surface and one on the garment facing surface, they would be typically arranged in such a way that the compartments 130 containing the absorbent material 110 from one storage layer are aligned with the compartments 130 containing the absorbent material 110 from the other storage layer in order to have the attachments from both layers adjacent to one another. In another alternative embodiment, however, the compartments 130 and the respective attachments are offset one another.

Figure 1D:
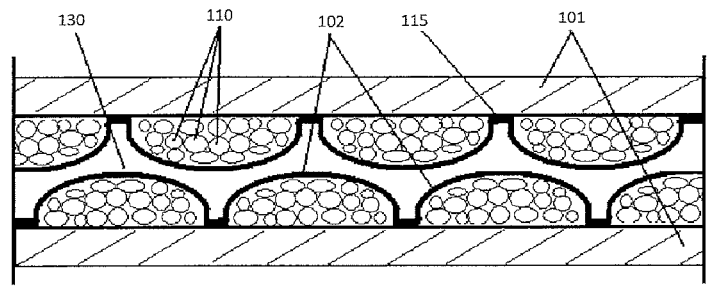
Figure 2:
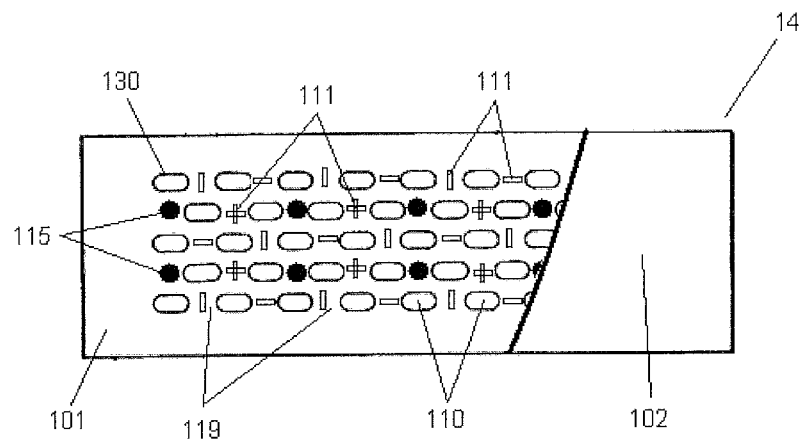
FIG. 2 provides a top view schematic illustration of an absorbent structure according to an embodiment of the invention.
Figure 3:
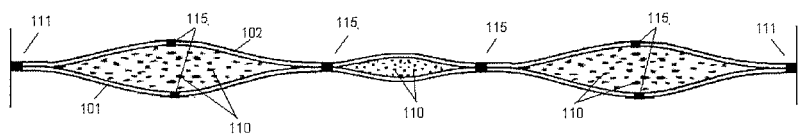
FIG. 3 provides a top view schematic illustration of an absorbent structure in a partially wetted state according to an embodiment of the invention, indicating substantial permanent primary attachments; and the gradual release by the still joined and already loosened temporary secondary attachments.

Referring to FIG. 1D, it has also been found that absorbent structures 14 can be formed by combining two or more layers of absorbent material 110. The absorbent structure 14 as shown comprises two layer of absorbent material 110, two carrier layers 101, and two auxiliary layers 102. When two discontinuous layers of an absorbent material 110 are used, they would typically be arranged in such a way that the pockets 130 containing the absorbent material 110 of one storage layer faces the pockets 130 containing the absorbent material 110 of the other storage layer. In an alternative preferred embodiment, however, the attachments are offset and do not face each other. Hence preferably, when two storage layers are joined, this is done such that the first carrier layer 101 of the first storage layer faces the auxiliary layer 102 of the second storage layer, while the auxiliary layer 102 from upper storage layer is situated on the wearer facing surface and the carrier layer 102 from lower storage layer is situated on the garment facing surface of the sandwiched structures.

Typical examples of methods used to join material and layers to each other are by way of example, but are not limited to, the use of an adhesive such as for instance pressure sensitive adhesive, curing, chemical links such as for instance hydrogen and covalent bonds or via the use of ultrasonic and/or other thermal, mechanical or thermo-mechanical attachment techniques such as for instance heat sealing, needling, air, entanglement, resistance and water jet pressure, and the like.

However, if the carrier layer 101 and the auxiliary layer 102 are solely attached to one another for example via an area of mechanical resistance or entanglement, or via an area on which the layers are fused together; without the need of any additional bonding or joining agent, no attachment media is provided. In a preferred embodiment, the primary attachments 111 and secondary attachments 115 are solely made up by ultrasonic thermo-sealing, which are preferably water-insensitive. Typically thermo-sealing areas of the primary attachments 111 are relatively large(r) in surface, tenacity and/or integrity (than the thermo-sealing area's of the secondary attachments 115), resulting in an absolute or relative high(er) separation force. In general, the attachments can come in various sizes and shapes, such as round, elliptic, rectangular or square shapes but it is preferred to provide them with rounded edges to inhibit the carrier layer 101 and auxiliary layer 102 from tearing apart during use. Preferably primary attachments 111 are arranged in a pattern consisting of rounded elements of which around 50% are oriented along an X-axis, and the remainder along a Y-axis. Combinations of elliptical-like shapes, such as uni-dimensional and bi-dimensional shapes serve as excellent primary attachments 111.

It is also preferred to design the attachments so that they have an average surface size of at least about 0.5 mm$^2$, preferably at least about 1.0 mm$^2$, 2 mm$^2$ or 3 mm$^2$, more preferably at least about 16 mm$^2$. Also the density of the attachments can vary, depending on the surface size of the individual attachments and desired separation forces. For attachments with a surface area smaller than 1 cm$^2$ for instance, it is recommended to use a density of at least about 100 per m$^2$. In another embodiment of this invention, the primary attachments 111 are arranged in a primary attachment grid composed of continuous lines so as to allow for additional liquid distribution and transport, for a high separation force and high resistance against the propagation of an eventual cracks or fissures in the pockets 130. The primary attachment pattern is carefully designed so that in a wetted state, the swollen material remains stabilized around the locations where it was restrained and/or immobilized in dry state. Failure to do so would result in breaking-up and/or displacement of the wet absorbent material, resulting in defective fluid management and to loss of performance, reduced fit and comfort, even full failure. The primary attachment pattern also accommodates the liquid management surface structures.

Apart from the primary attachments 111 and secondary attachments 115, there are also unattached regions 119, where there is substantially no attachment, bond and/or joint between the carrier layer 101 and auxiliary layer 102, thereby providing pockets 130 in which the absorbent material 110 can be located to form well-designed clusters. The primary attachments 111 correspond with a primary attachment grid, whereas the secondary attachments 115 correspond with a secondary attachment pattern. As the secondary attachment pattern will release under the swelling force of the absorbent materials and/or under the influence of water, the secondary attachment 115 should have a relative low separation force is use. Preferably the separation force necessary to break the attachment will be lower than about 5.0 N/cm, more preferably lower than about 2.5, 2.0 or 1.0 N/cm, even more preferably lower than about 0.75, 0.5 or 0.25 N/cm and most preferably lower than about 0.20 or 0.10 N/cm in use.

The bonding strength, such as for example the dry strength, wet burst strength and/or wet strength, should suffice all required parameters of the absorbent structure and will amongst others depend on the absorbent article, its product size and shape and the required duration of the usage and performance. The specific structural and functional strength of the attachments in between the auxiliary layer and the carrier layer and/or the different wet strengths in between the attachments of the primary attachment regions and the secondary attachment regions allows for more efficient design and usage of the absorbent structures leading to more, faster and enhanced absorption, distribution and retention of liquids, such as bodily exudates. Moreover it also allows for better and controlled liquid wicking and dispersion within said absorbent storage layer, leading to more efficient and effective fluid communication or transport from the less absorbent area's (e.g. saturated) to the more absorbent area's (e.g. unsaturated).

In one embodiment of this invention, a specific hydro-soluble or water-sensitive secondary attachment is used, for instance in the form of an adhesive as secondary attachment medium. In a more preferred embodiment however, both layers are thermo-sealed together, most preferably by wet-insensitive ultrasonic bonding, without any synthetic attachment admixtures. The thermo-sealing areas of the secondary attachments 115 being relatively small(er) in surface, tenacity or integrity (than the primary attachments 111) resulting in an absolute or relative low(er)

separation force. The thermo-sealing areas can come in various sizes and shapes, but it is preferred to provide at least one sharp edge to facilitate the carrier layer 101 and auxiliary layer 102 to tear apart. Combinations of circle-like shapes, such as round and dot shapes are also preferred as secondary attachments 115. Elimination of attachment media leads to lower raw material and production costs and environmental/sustainable absorbent structures. It is furthermore advantageous to use thermo-sealing as attachment means, rather than using adhesive, as the production cost is then usually substantially lower and one can claim to be 'adhesive-free', a claim which is important to environment-conscious consumers.

As carrier layer 101 and/or auxiliary layer 102, having a typical basis weight in the range of 3-400 gsm, more preferably 5-75 gsm, one can choose from a variety of materials such as but not limited to high-lofts, airlaids, rigid, stretchable or elastic non-wovens or a woven fabric, wetlaid material such as cellulose tissue, paper, film, tissue, perforated films, foam material, thermoplastic material, layers of adhesive or whatever material suitable within the absorbent structure 14. The sandwich layers can be made out of the same or different materials having different compositions, weights and/or structures. In a preferred embodiment, at least one of the layers is liquid permeable over at least part of its surface so that liquids can be taken up in the Z-direction. In another embodiment both the carrier layer 101 and the auxiliary layer 102 are liquid permeable. In yet another preferred embodiment, one of the layers is a liquid permeable non-woven material and the other layer is a substantially liquid-impervious and possibly breathable polyethylene (PE) film, whereby the non-woven is positioned at the expected liquid flow such as the wearer-facing side of the absorbent structure 14 in case of an absorbent article such as a diaper, and the PE film is positioned away from the expected liquid flow such as the garment-facing side of the absorbent structure in case of an absorbent article such as a baby diaper. In this case, one could for instance select 22 gsm polypropylene non-woven material from Albis and 20 μm breathable polyethylene film from Nuova Pansa. The use of the terminology 'carrier layer' by no means implies that the fabric should be strong enough to support the structure or should be situated at the lower region of the absorbent structure 14. Nor does 'auxiliary layer' imply that this layer should have a lesser function or should by analogy be situated at the upper region of the absorbent structure 14.

In an alternative embodiment the carrier layer 101 and/or auxiliary layer 102 can be an adhesive in combination with other immobilisation diluents such as tackifying resins, plasticizers and additives such as antioxidants, but could well be any other composition able to substantially immobilise absorbent polymer material 110 within the absorbent structure 14 according to the invention. Some immobilisation materials are thermoplastic others are not, while some initially thermoplastic materials may lose their thermoplastic behaviour due to a curing step, e.g. initiated via heat, UV radiation, electron beam exposure or moisture or other means of curing, leading to the irreversible formation of a cross-linked network of covalent bonds. The adhesive and binders are preferably applied by a nozzle system. Preferably, a nozzle system is utilised which can provide a relatively thin but wide curtain of binder. This glue curtain can be continuous or discontinuous, so as to be applied in a homogeneous or heterogeneous surface or can be applied in various combinations of lines, grids, spirals, figures, spots, dots, etc. either in a determined or undetermined location of the target surface and/or any combination thereof. Those materials having lost their initial thermoplastic behaviour are herein also understood as immobilisation materials. It has been found that compositions most useful for immobilizing absorbent polymer materials are those which combine controlled cohesion and adhesion behaviour. Adhesion is preferred to ensure that the layer maintains sufficient contact with the absorbent polymer material 110. Cohesion ensures that the attachment does not unintentionally detach or keeps attached, in particular in response to external forces, and namely in response to strain. The attachments are subject to external forces during usage and when the absorbent structure swells due to the acquired liquid.

In an alternative embodiment of the present invention the absorbent structure 14 comprises an additional distribution layer 100a which helps to additionally absorb, distribute and transport liquids and having a capability to disperse the liquid permeating within said distribution layer 100a from the less absorbent area's (e.g. saturated) to the more absorbent area's (e.g. unsaturated).

In an alternative embodiment of the present invention the absorbent structure 14 comprises an additional liquid-impermeable, either hydrophilic or hydrophobic, wicking layer 100b which helps to wick and transport liquids and having a capability to disperse the liquid over the surface of said wicking layer 100b from the less absorbent area's (e.g. saturated) to the more absorbent area's (e.g. unsaturated).

In an alternative embodiment of the present invention the absorbent structure comprises an additional thermoplastic immobilisation layer such as thermoplastic adhesive or binder (e.g. hot-melt) which helps to immobilize the absorbent materials 110 within the absorbent structure 14.

However it should be understood that in the alternative embodiments hereof, the carrier layer 101 and/or auxiliary 102 can have the same or similar properties as the distribution layer 100a and/or wicking layer 100b and thus be uniform therewith to form the actual absorbent structure 14. For reasons of clarity the embodiments down below will be explained so as the distribution layer 100a and wicking layer 100b are complementary to the carrier layer 101 and the auxiliary layer 102 within the absorbent structure 14. Although such distribution layer 100a or wicking layer 100b is preferably located at the garment facing side of the absorbent polymer material area, it is understood that the orientation of the absorbent structure 14, although not preferred, can also be re-orientated so as to locate the distribution layer 100 or (for instance perforated) wicking layer 100b at the wearer facing side of the absorbent polymer material area, while various combinations and variations are of course also possible. The distribution layer 100a and/or wicking layer 100b can for instance also have access means, such as perforations, holes, channels, openings, fixed or releasable pockets and the like.

Due to the specific absorbent capacity of the distribution layer 100a, the liquid around the attachments in between the pockets 130 will be drawn up into the distribution layer 100a and will spread out throughout the rest of the distribution layer 100a. In a preferred embodiment of the invention, the liquid wetting of the distribution layer 100a will therefore also contact the lower side of the absorbent polymer material area possibly fully or partially closed off by the upper gel-formation and/or -blocking. The absorbent material held in the compartments 130 will thus advantageously also be contacted from the lower side by redirecting the liquid from the upper side through the distribution layer 100b into the absorbent material 110, such as absorbent particulate polymer material.

Due to the specific distribution capacity of the wicking layer 100b, the liquid which comes in contact with the substantially liquid-impermeable wicking layer 100b will readily spread out over said surface to also contact the absorbent materials 110 located at the adjacent and/or lower surface of the absorbent polymer material area, being the side opposite the major surface side where the liquid was first deposited. The distribution, transport and absorption of the liquid is thus greatly improved and this speedy distribution will help to avoid large amounts of unbound quantities of liquid within helping to prevent absorbent article failure and high rewet values. Providing an additional and more direct co-extensive wicking, dispersion and transportation of liquid to the still more absorbent underused pockets and compartments of the absorbent structure increases effectiveness and efficiency of the available absorbent materials 110. The presence of unbound liquid droplets leading to leakages, high rewet values and discomfort are thereby minimized.

This distribution layer 100a has preferably an absorbing capacity of at least about 1, 2, 3, 4 or 5 $g/m^2$, preferably about 10 $g/m^2$, more preferably about 20 $g/m^2$, more preferably at least about 35 $g/m^2$, most preferably at least about 50 $g/m^2$, or 100 $g/m^2$. Preferably the distribution layer 100b is presented in the form of a substantially continuous sheet of cellulosic fibers, such as a nonwoven or a sheet of paper or tissue. In a preferred embodiment, it has a basis weight range where the low limit of the range is about 1, 2, 3, 4, 5, 6, 7, 8, 9, 10 $g/m^2$ per ply, about 13 $g/m^2$ per ply, or about 15 $g/m^2$ per ply. The high limit of the basis weight range is about 150 $g/m^2$ per ply, 100 $g/m^2$ per ply, about 40 $g/m^2$ per ply, or about 25 $g/m^2$ per ply. Suitable wicking layer 100b are for instance coated polyethylene or polypropylene films, with a total thickness of such film is usually in the range from 5 to 1500 μm, preferably from 10 to 500 μm, for instance a being corona-treated, hydrophilic, micro-embossed PE film in the 15-22 μm thickness range.

The substantially liquid-impermeable wicking layer 100b is for instance provided by a substantially continuous layer of foil, film, closed foam, plastic or similar substantially liquid-impermeable materials, media and/or layers. The effect of providing the substantially liquid-impermeable wicking layer 100b in the form of a substantially continuous layer of film or foil is that a substantially impervious barrier is provided. The provision of a film or foil is advantageous compared to the use of a pervious layer, such as for instance a non-woven material, as in contrast to such non-woven material the film or foil is not comprised of fibers. Hence, it is not possible that fibers are torn upon exertion of a force onto the film or foil, for instance during movement and/or liquid uptake process (e.g. swelling and expansion of the absorbent material such as super absorbent polymers). Opposed to non-woven materials, such wicking layer 100b does not contain unintentional open spaces and cavities in which unbound quantities of liquid may be stored, thus not leading to an increased risks of leakages and augmented rewet with reduced comfort and fit.

In a preferred embodiment the carrier layer 101, auxiliary layer 102, distribution layer 100a and/or wicking layer 100b can be fully or partially hydrophilic or hydrophobic. In a more preferred embodiment, they are provided with a hydrophilic or hydrophobic coating. Combinations thereof are hereby also encompassed. The effect of providing such layers with coatings is that the properties of the layer can be modified according to the intended use. For instance, synthetic materials that are inherently hydrophobic such as polyethylene (PE) or polypropylene (PP) can for instance be provided with a coating layer such that the resulting material has a contact angle of less than 50°, preferably less than 35°, more preferably less than 25°, still more preferably less than 20°, most preferably less than 15°, for a water droplet lying thereon. For instance, materials that are inherently hydrophilic can be provided with a hydrophobic coating layer such that the resulting material shows hydrophobic properties. This may be advantage in the fact that a cheap base layer, itself not displaying the desired property can be adjusted on at least one of its sides to display the desired property, thereby providing cost savings. The coating can be applied by a commonly used suitable process, for example with a slot coater, or by a spray process. It is particularly preferable to apply the coating by the reverse gravure-roll process, which can apply an extremely homogeneous coating with application weights of from 0.5 to 5.0 g/m². The thickness of the coating on the finished film is preferably from 3 to 1000 nm, in particular from 30 to 200 nm. Obviously such coating can also be applied continuously, substantially continuously, partially or at discreet locations possibly showing multiple flow enhancing patterns and/or shapes depending on the desired end product and features.

The distribution layer 100a and/or wicking layer 100b used may differ in basis weight, thickness, composition or other properties. If provided as multiple plies, they can be passively bound or joined, or a certain amount of adhesive or other attachment means could be added to provide additional adhesion to portions of the component plies. For example, needling, embossing, or other thermal or mechanical bonding means could also be used to actively bond the substantially continuous layer near some or all of the edges of the sheet, thereby providing increased resistance to undesired delaminating of the component plies. Joining may also be done by ultrasonic bonding or autogenous bonding, or other bonding methods known in the art. For example, if the edges of the ply or layers are coextensive with the edges of the outer plies, adhesive bonding and heat sealing adhesive may not provide active bonding, depending on the adhesive used and the surface energy characteristics of the ply. In this case, mechanical bonding may be more desirable, for example by mechanical bonding at a mechanical bonding station after formation of the multiple plies. Depending on the structural and functional requirements the bonding parameters may be adjusted so as to obtain the most suitable dry and wet strength values. If desired, multiple plies of the substantially continuous layer may be joined and embossed. If desired, the plies may be joined together using knob-to-knob or know-to-flat surface embossing as is known in the art. Alternatively, the multiple plies may be embossed using nested embossing. The substantially continuous layer may manifest various physical characteristics.

The distribution layer 100a preferably has an absorbency ranging from about 0.1 g to 3 g water per g of distribution layer, preferably from about 3 to 7 g, more preferably from about 7 to 10 g and preferably the absorbency is higher than about 10 g water per g of distribution layer 100a. The distribution layer 100a typically has an absorbent capacity of at least about 5-10 g/m², preferably at least about 30 g/m², more preferably at least about 50 g/m², more preferably at least about 75 g/cm², preferably at least about 100 g/cm² or 150 g/cm². Preferably distribution layer 100a is presented in the form of a substantially continuous sheet of cellulosic fiber, such as a sheet of paper, tissue or a drylaid, airlaid or wetlaid material.

Despite the high absorbency and distribution capacities of the substantially continuous layer, the bulkiness of said layer is absolutely and relatively limited, for instance in comparison with absorbent articles and absorbent structures from the art allowing the envisaged thinner, more flexible and comfortable structures.

For the present invention, the substantially continuous layers can have a basis weight ranging from about 5 g/m² to about 150 g/m². Preferably, the substantially continuous layer can have a basis weight ranging from about 13 g/m² to about 23 g/m². More preferably, the substantially continuous layer can have a basis weight of about 16-18 g/m². The substantially continuous layers preferably have sufficient strength to perform their intended tasks. Preferably, the substantially continuous layer maintains its integrity when partially or fully wetted, so that the distribution of liquids to and the immobilization of the absorbent materials may be accomplished. The distribution layer preferably has a wet burst strength ranging from a lower limit of about 50-75 g and preferably about 200 g, to an upper limit of about 800 g, more preferably about 600 g, and most preferably about 400 g. This is advantageous as it provides the layer with a good combination of absorbency and wet strength. The substantially continuous layer can be creped, uncreped, or wet micro-contracted tissue webs. The substantially continuous layer may be nonwoven, paper or tissue consisting essentially of cellulosic papermaking fibers. Optionally, the substantially continuous layer may be foreshortened, and/or contain synthetic fibers. In a preferred embodiment of the absorbent article according to the invention, the bonds, joints and connections from the distribution layer 100a are not permanent so that the bonds may partially break, detach and/or disintegrate during wetting.

In a preferred embodiment of the invention, portions of the carrier layer 101 and/or auxiliary layer 102 bond or join to portions of the distribution layer 100a; the distribution layer 100a together with one or more layers from the absorbent structure 14 cavities for the immobilization of the absorbent material, preferably absorbent particulate polymer material. The bonding strength should suffice the required parameters of the absorbent structure and will amongst others depend on the product size, shape, category and required duration of the usage and performance.

The pockets 130 can have a regular shape, irregular shape or combination thereof. Preferred shapes of the pockets 130 are circular, elliptic or square with a diameter, radius or side larger than about 0.1 mm, 0.2 mm, 0.3 mm, 0.4 mm, 0.5 mm, more preferably larger than about 0.75 mm and smaller than about 60 mm, more preferably larger than about 1.0 mm and smaller than about 40 mm, more preferably lager than about 2.0 mm and smaller than about 20 mm and most preferably larger than about 3.0 mm and smaller than about 15 mm. The absorbent material 110 does not necessarily fill the pockets 130 entirely as it might be advantageous to leave some void space adjacent the absorbent material 110 in the pockets 130 or leave some pockets 130 partially or completely empty. The inventor has found that in particular rectangular shaped pockets 130 with a side of about 10 mm are particularly advantageous to be used as building blocks for the final compartment sizes within the wetted and released absorbent structure 14, as they are easier to manufacture at high production speed while still allowing meticulous controlling of the prescribed bonding strength of the primary and secondary attachments.

Preferably the distribution of absorbent polymer material is profiled and most preferably profiled in the longitudinal direction. Hence, along the longitudinal axis of the absorbent structure, which is normally coincident with the longitudinal axis of the absorbent article, for example of the baby diaper, the basis weight of the absorbent polymer material will change. Preferably the basis weight of absorbent polymer material in at least one freely selected first square measuring 1 cm×1 cm is at least about 10%, or 20%, or 30%, 40%, 50% up to more than 100% higher than the basis weight of absorbent polymer material in at least one freely selected second square measuring 1 cm×1 cm. Preferably the criterion is met if the first and the second square are centred about the longitudinal axis.

The primary attachments 111 have to substantially resist the frictions and strain during normal use of the absorbent structure 14 and the forces resulting from the expanding and swelling absorbent material 110 caused by the liquid uptake. Since the bonding strength of water-sensitive attachment means would be very hard to control during usage conditions, they are preferably not used within an absorbent structure 14 according to the present invention. Preferably the dry and/or wet separation force necessary to release the primary attachment grids in between the carrier layer 101 and auxiliary layer 102 will be higher than about 0.05 N/cm or about 0.75 N/cm, more preferably higher than about 0.1, N/cm, 0.2 N/cm or 0.3 N/cm, even more preferably higher than about 1.0 N/cm, 1.5 N/cm, 2.5 N/cm and most preferably higher than about 3-5 N/cm. The attachment grids and patterns can consist of various sub-regions, corresponding to different separation forces.

Figure 4:
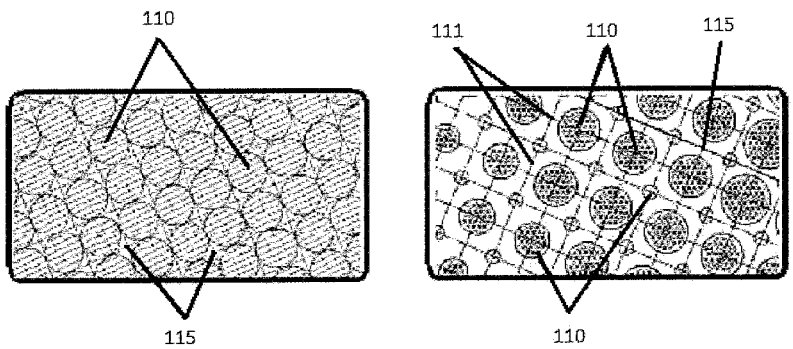
FIG. 4 provides a top view schematic illustration of differently located and sized clusters of absorbent material according to an embodiment of the invention.
Figure 5:
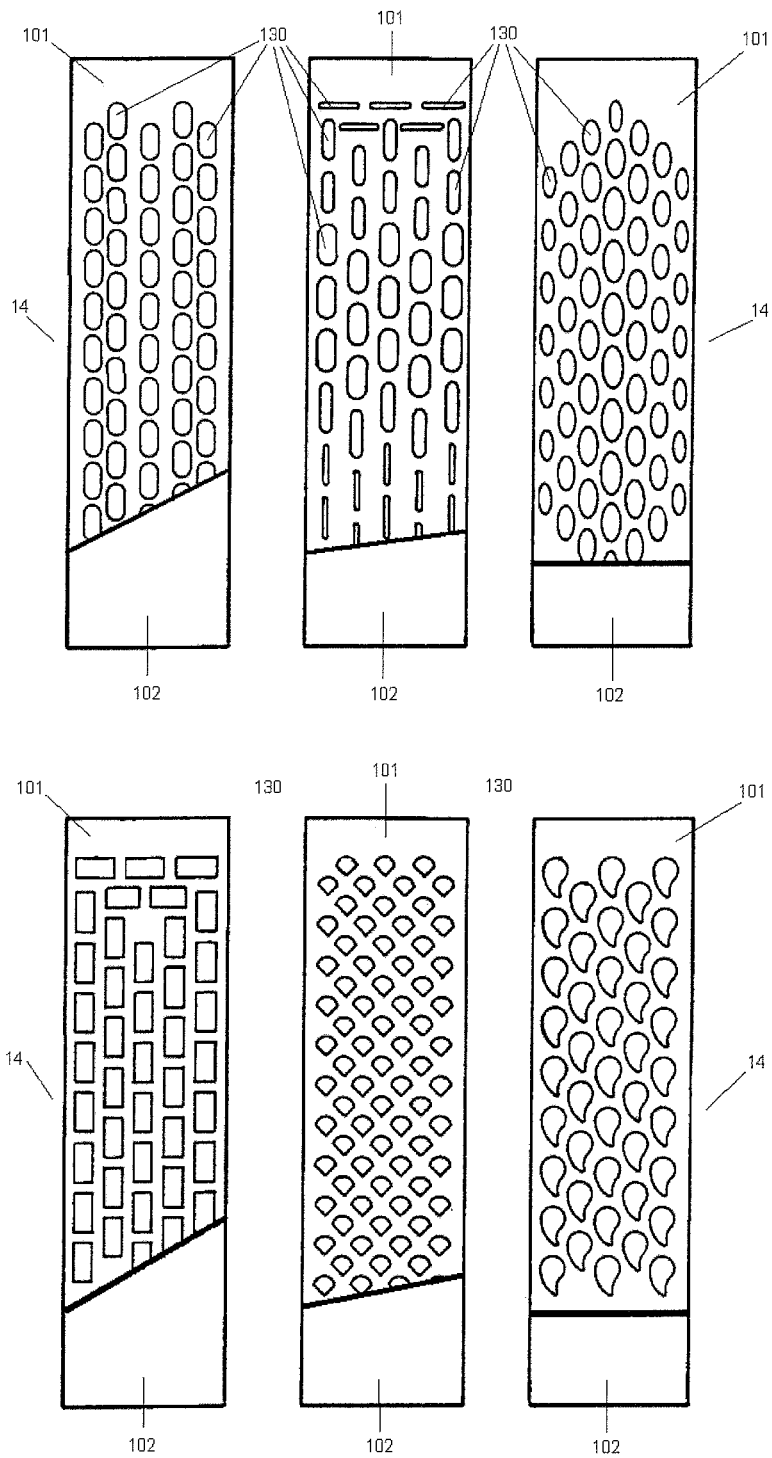
FIG. 5 provides top view schematic illustrations of an absorbent structure according to an embodiment of the invention indicating different cluster patterns.

As can be seen from FIGS. 4 and 5, the absorbent material pattern formed in between attachments can be random or regular, substantially continuously connected or isolated, fully-covering or partially covering and/or any other suitable combination. Preferably the absorbent material regions consists of several clusters of absorbent material 110, surrounded by areas where substantially no absorbent material 110 is present, which can act as additional distribution and transport channels facilitating the flow of liquid away from the point of insult and towards available clusters of absorbent material 110. Weight distribution of absorbent material 110 over the absorbent structure 14 can be regular across the major surface or can profiled, i.e. the basis weight of the absorbent material 110 may change depending on its position in the absorbent structure 14, for instance very desirable for use in diaper and pants cores where one would like to concentrate absolute and/or relative more absorbent material 110 near the point of liquid insult. Suitable materials such as for instance highly permeable SAP are offered by Evonik, BASF and Nippon Shokubai. Although preferably the absorbent polymer material form up to 100% of the absorbent material 110 it can also be used in combination with other materials such as for instance cellulose fibres or fluff pulp, however preferably the amount of fibrous materials would not make up more than about zero to 40 weight percent. Fully cellulose free structures benefit maximal of this invention.

The total absorbency and swelling capacity of an absorbent polymer materials are controlled by the type and degree of cross-linkers used to make the hydrogel. Low density cross-linked SAP generally has a higher absorbent capacity and thus typically is able to swell to a relatively larger degree. These types of SAP also have a softer and more sticky gel formation. High density cross-linked SAP generally exhibits lower absorbent capacity and swell to a relative lower degree, but the gel's strength is firmer and can maintain particle shape even under modest pressure. Absorbent polymer material are commonly made from the polymerization of acrylic acid blended with sodium hydroxide in the presence of an initiator to form a poly-acrylic acid sodium salt (sometimes referred to as sodium polyacrylate). This polymer is the most common type of SAP made in the world today. Other materials are also used to make a SAP, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile to name a few. The latter is one of the older SAP forms created.

All these SAP technologies have been common in the absorbent structure industries for many years and are well-known by the persons skilled in the art. Generally, SAP manufacturers can vary several process parameters and finishing specifications such as cross-linking level and particle size and offer the absorbent article designers a wide choice of absorbent polymer material products ranging from SAP with low swelling capacity to high swelling capacity, and from slow swelling behavior to fast swelling behavior. By making the appropriate choice, one can design absorbent structures with a combination of such different SAP concepts, where preferably the fast swelling SAP and/or SAP with high swelling capacity would be used in the areas which would have to act as heights or embankments, while preferably the slow swelling SAP and/or SAP with low swelling capacity would be used in the areas which would have to act as depressions or canals.

In an alternative embodiment of this invention, one can use higher amounts of SAP in certain areas, while other areas would be free from SAP or have relative limited amounts of SAP so that, when wetted, the areas with relative higher amounts of SAP would swell to form heights while those without or with relatively limited amounts of SAP would form the depressions.

Figure 6A:
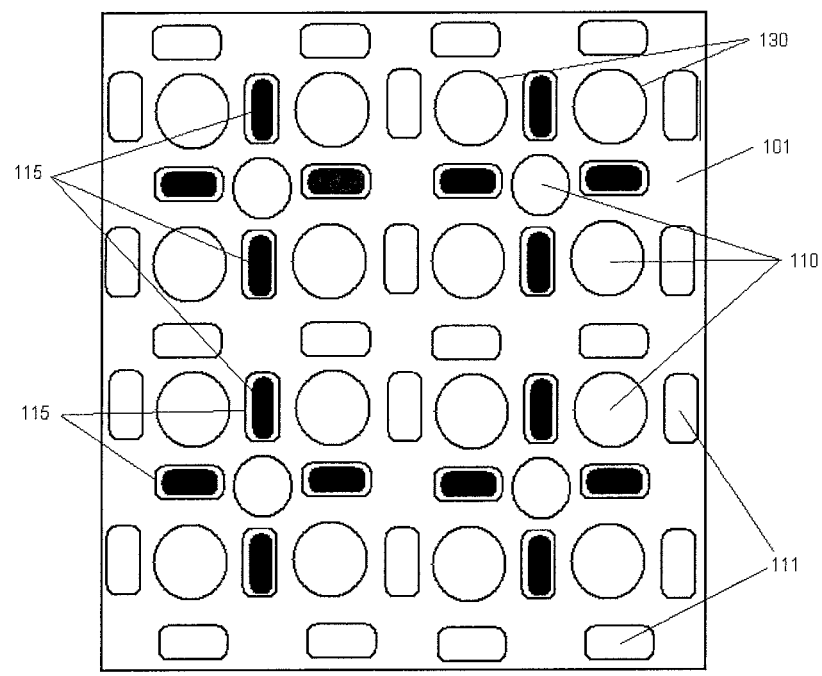
FIG. 6A-B provides top view schematic illustrations of absorbent structures according to an embodiment of the invention in intact (A) en loosened (B) state.
Figure 6B:
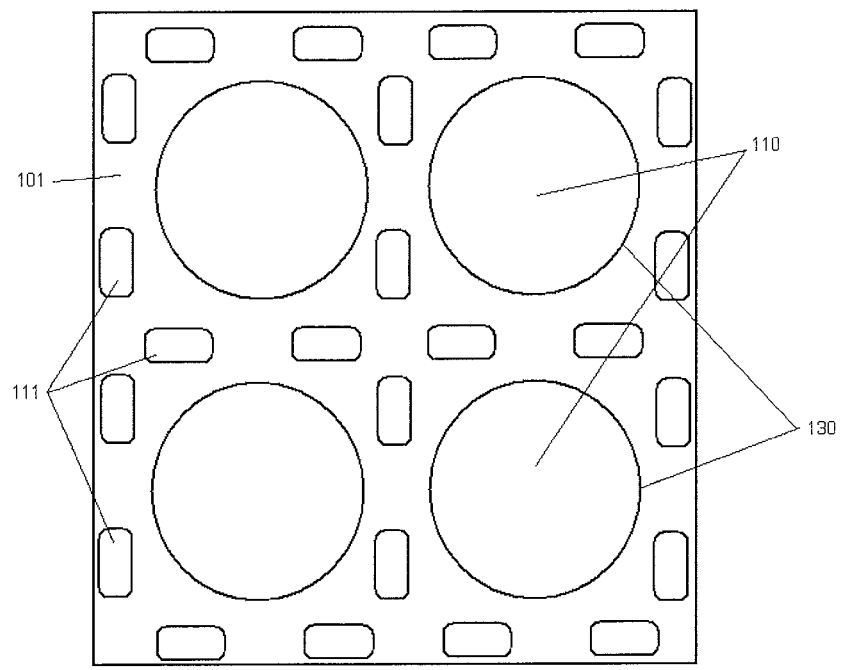

The breaking of the secondary attachments 115 allows the carrier layer 101 and/or auxiliary layer 102 to deform, stretch and change shape. As a result, the minimal volume pockets 130 are able to expand to an intermediate volumes and finally to maximum volume compartments so as to accommodate the extra volume resulting from the highly expandable absorbent material 110. Thus, as seen in FIG. 6, an absorbent structure 14 with expandable pockets 130 with additional activated free swell volume is created, allowing the absorbent material 110 to be more effectively and efficiently used and reducing the risk of bursting of one or more sandwiching layers. The extra volume created by the expanding pockets can for instance be about 1% to 5% of the original volume. Preferably it is higher than about 5% to 25%, more preferably higher than about 25% to 50%, most preferably higher than about 50% or 100% of the original volume. In an alternative embodiment, the absorbent structure 14 consists of multilayered sandwich structures where on the first sandwich structure of carrier layer 101—absorbent material 110—auxiliary layer 102, additional layers of absorbent material and/or complementary layers can be added. Such structures can provide good liquid absorption whilst retaining product integrity, in dry and wet state.

Figure 7:
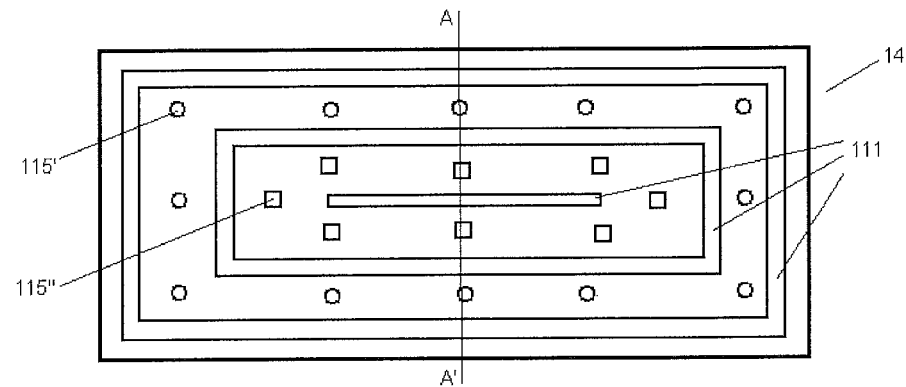
FIG. 7 provides a top view schematic illustration of an absorbent structure according to an embodiment of the present invention, illustrating a built-in phased expansion by primary attachment grids and secondary attachment patterns.
Figure 8:
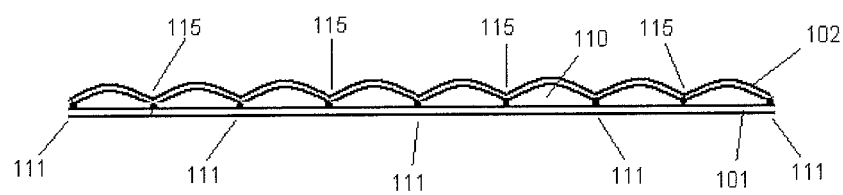
FIG. 8 provides a cross-sectional schematic illustration of a dry absorbent structure having phased expansion according to an embodiment of the invention.
Figure 9:
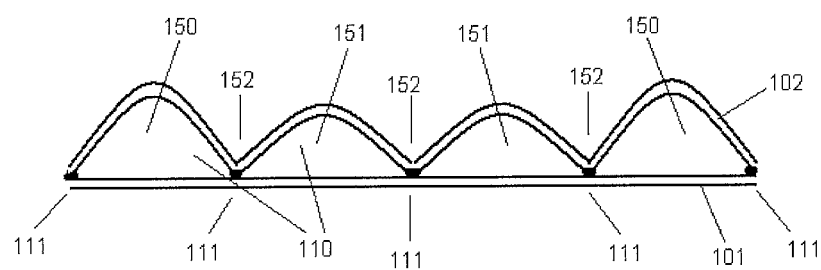
FIG. 9 provides a cross-sectional schematic illustration of a wetted absorbent structure having phased expansion according to an embodiment of the invention.

FIGS. 7, 8 and 9 show embodiments according to the invention where secondary attachment 115 consist of weaker secondary attachments 115' and stronger secondary attachments 115" where weaker secondary attachments 115' loosen faster than the stronger secondary attachments 115". The different functionalities in between the primary attachments 111 and secondary attachments 115 in combination with the bonding strength differentiation in between weaker secondary attachments 115' and stronger secondary attachments 115" allows the design of an absorbent structure 14 with a predetermined, controlled and/or phased volume-expansion of the absorbent structure for ultimate fluid management.

In a more preferred embodiment, the absorbent structure 14 consists of weaker secondary attachments 115' at the periphery of the absorbent structure 14 allowing for primary and easy expansion of the absorbent material 110 adjacent the longitudinal and/or end edges of the absorbent structure 14, thereby creating containment or anti-leakage barriers within the absorbent structure 14. Such a particular internal incorporated barrier construction has great pre-usage, usage and post-usage advantages for the construction of disposable absorbent hygiene articles such as garments, diapers or pants. As shown in FIGS. 7, 8 and 9, the weaker secondary attachment 115' loosen to form first barriers or embankments 150, whereas the stronger secondary attachments 115" form the only later arising secondary barriers or embankments 151. The substantially wet-resistant permanent primary grids form canals 152 in between the first embankments 150 and/or the secondary embankments 151. Due to the time difference between the formation of the first embankments 150 and the respective secondary embankments 151, the first embankments 150 will contain the liquid inside the product, where it can be distributed via the canals 152 and it will further be stored in and contained by secondary embankments 151. Obviously combinations and variants are possible.

In a preferred embodiment, one can for instance create embankments in such a way to obtain a pocket being an elongated or rounded depression, substantially surrounded by embankments. Such embankments can be lowered or interrupted to create one or more in- or outlets. The void space inside the pocket can especially be used to store liquids, solids and/or liquids of high viscosity. In baby diaper or adult incontinence products, such additional embankments can act as a cushion, providing comfort, keeping skin away from stool and preventing stool to be pushed out of the absorbent article when the wearer exerts pressure, e.g. by sitting, on the product. Various shapes, sizes, locations and combinations can be envisaged. In a more preferred embodiment of this invention, one can create a stool containing pocket since it is known that infant stool can be very 'liquid-like'.

Human feces (or human faeces), also known as stools, is the waste product of the human digestive system and varies significantly in appearance, depending on the state of the whole digestive system, influenced and found by diet and health. Normally stools are semisolid, with a mucus coating. The Bristol Stool Chart or Bristol Stool Scale is a medical aid designed to classify the form of human feces into seven categories. Sometimes referred to in the UK as the "Meyers Scale," it was developed by K. W. Heaton at the University of Bristol and was first published in the *Scandinavian Journal of Gastroenterology* in 1997. The form of the stool depends on the time it spends in the colon.

The seven types of stool are:
1. Separate hard lumps, like nuts (hard to pass).
2. Sausage-shaped but lumpy.
3. Like a sausage but with cracks on its surface.
4. Like a sausage or snake, smooth and soft.
5. Soft blobs with clear cut edges (passed easily).
6. Fluffy pieces with ragged edges, a mushy stool.
7. Watery stool, entirely liquid.

Types 1 and 2 indicate constipation, with 3 and 4 being the "ideal stools" especially the latter, as they are the easiest to pass, and 5-7 being further tending towards diarrhea or urgency. Stool from small children, and especially younger babies, can often be classified in type 5, 6 or 7 and may be referred to as 'liquid stool'.

Due to its high viscosity, the liquid stool does not significantly get absorbed through the topsheet of the absorbent article, and often gives rise to a leakage. Leakage of stool from an absorption article is even less appreciated than urine leakage, as the former provides even more inconvenience to the wearer and caretaker, and provides more problems for health and hygiene. By creating the superficial liquid management system such as for instance a stool pocket, one can create a void space which can be filled with stool. Contained by the embankments, the stool will substantially remain in place. In order for a stool pocket to perform optimally, the depressions should be at least 5%, preferably 10%, more preferably 15% or most preferably at least 20% lower than the heights in the rear section of the product.

In alternative embodiment, at least one of the carrier layers 101 or auxiliary layer 102 is made out of an elastic or stretchable material, allowing for at least a first volume expansion before the gradually increasing expansion force of the wetting and swelling absorbent materials 110 accommodates the eventual breaking of the wet secondary attachments 118.

Figure 10A:
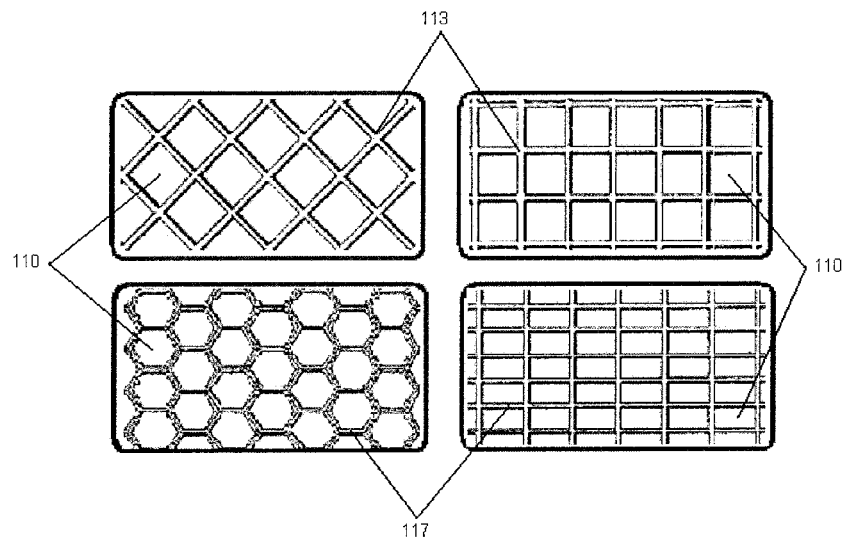
FIG. 10A-B provides a top view schematic illustration of absorbent structures according to the invention, in dry state with a plurality of smaller-sized pockets (A) and in wet state with fewer and larger-sized compartments (B).
Figure 10B:
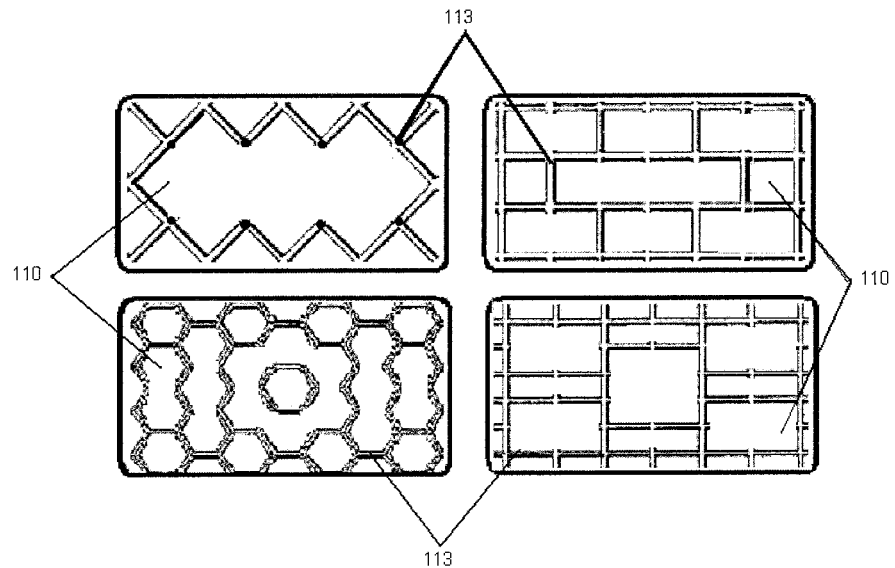

With reference to FIG. 10A-B the primary attachments 111 from the absorbent structure 14 correspond with a predefined primary bonding grids 113, whereas the secondary attachments 115 from the absorbent structure 14 correspond with a secondary bonding pattern 117. These grid and pattern shapes are developed in light of the desired structural and functional features. Obviously these grids and patterns merely act as illustrations and examples as various combinations, shapes and sizes are of course possible in relation to desirable absorbent structures. Referring to FIG. 10A, the lines of these patterns may be disposed regular or irregular, continuous or discontinuous, coextensive with the entire surface of the absorbent structure or only part thereof and any combination and/or derivations thereof. These lines may be aligned with the longitudinal, transversal or diagonal axis of the absorbent structure 14 or alternatively any angle in respect of such axis. It has been found that, that a continuous disposition of these lines throughout the absorbent structure 14 creates additional channels and ducts which help the fluid transport from the point of liquid contact to the rest of the absorbent structure via mass flow allowing better and more spread out immediate liquid management via capillary flow locally. Care however should be taken not to allow channelling of liquid to the very side of the absorbent structures to avoid leakages upon time of insult, preferably they will thus guide the liquid to the entire surface of the absorbent structure with the exception of the outer edges thereof. Another preferred pattern for grids and patterns comprises polygons, for example pentagons and sexangles or a combination thereof. Also irregular patterns are possible. In essence those grids and patterns are preferred which allow optimal packaging of absorbent particulate material in dry smaller pockets 130 while allowing ideal and maximum volume expansion to bigger compartment in wet state taking in mind the thin and flexible absorbent structures are envisaged. Too much loss of pocket and/or compartment volume in light of primary and secondary attachment grids and patterns in respective dry and wet stat is preferably avoided.

Referring to FIG. 10B, exemplary absorbent structures are shown with intact primary bonding grids 113 and released secondary pattern 117 leading to the bigger and fewer compartments as opposed to the plurality of smaller pockets 130 formed by the intact primary attachments 111 and secondary attachments 115 (FIG. 10A).

The invention provides use of an absorbent structure according to an embodiment of the invention in an absorbent product, selected from the list of coffee pads, disposable body warmers, sheet formed detergent article, filter material, insulation material, make-up pads, anti-septic wads, feminine hygiene garments, baby diapers, baby pants, adult incontinence garments, preferably said absorbent article is a feminine hygiene garment, baby diaper, baby pants or adult incontinence garment. The construction of such commercially available products is well-know from the art.

The absorbent structure claimed according to the present invention is thin and flexible, and thus has a low flexure-resistance. The flexure-resistance of the absorbent structures is measured by the Peak Bending Stiffness as determined by the test which is modelled after the ASTM D 4032-82 Circular Bend Procedure, the procedure being considerably modified and performed as described in EP0336578B1. In a preferred embodiment of the absorbent article of the invention, the absorbent structure has a flexure-resistance of less than 500.0 grams, more preferably less than about 250.0-350.0 grams, and still more preferably less than about 175.0 grams and most preferably less than about 130.0 or 100.0 grams. Thus, the absorbent structure of the present invention is highly flexible and conforms very well to the various shapes of the urogenital region. Use of an absorbent structure with this low a flexure-resistance has for effect that an easily flexible absorbent articles can be provided. This feature is advantageous as such a structure will easily ply and allow the structure to follow a body shape, and thus wearer fit and comfort.

The absorbent structure claimed according to the present invention has superior immobilisation characteristic in dry and wet state and the minimum wet immobilisation values as measured by the shaker test weight retention as determined by the Wet Immobilisation test as described in US Patent Application 20070167928 are very favourable. In a preferred embodiment of the absorbent structure of the invention, the absorbent structure has a wet immobilization of more than 60 wt %, preferably more than 70 wt %, more preferably more than 80 wt %, and most preferably more than 90 wt %. Such absorbent structure has an increased loading capacity and an improved absorption capacity.

Figure 11:
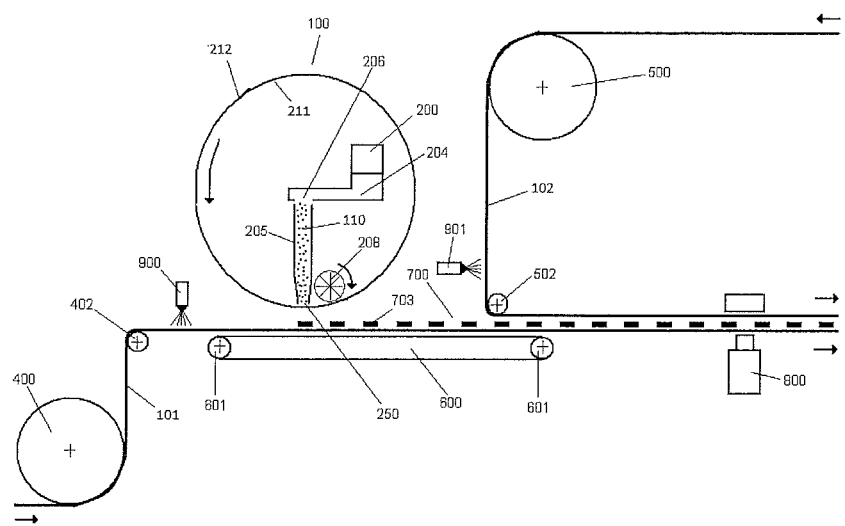
FIG. 11 provides a schematic process for manufacturing absorbent structures according to the invention.

With reference to FIG. 11, a method and apparatus is illustrated for forming a composite structure 700 according to the present invention, having a plurality of discrete particulate material clusters 703 which are preferably discretely distributed and deposited on a carrier layer 101 and contain selected quantities of particulate material 703. The representatively shown apparatus includes a particulate material supplying means 200 for providing absorbent materials 110 towards carrier layer 101. A web supplying means 400 and web transport means 402 provides a carrier layer 101 and a support means 600 via guiding means 601 and 602 moves the carrier layer 101 adjacent a depositing means, preferably provided in the form of a substantially endless rotating drum 100. A material supply means 200 direct absorbent material 110 by way of a dosing system 204 and a feeding tube 205 towards the a proximal opening 206. Optional brushing means 208 help to 'right-fill' the clustering means 250. The depositing means 206 preferably having clustering means 250 with a pattern of perforations arranged to form and provide a desired depositing pattern of particulate material clusters 703 onto the carrier layer 101. The support means 600 is preferably in substantial contact with the support surface 412 of the carrier layer 101. The support means 600 preferably ensures a close enough connection in between the deposit surface 411 of the carrier layer 101 and clustering means 250 to prevent unwanted migration of the particulate materials 110 from the carrier deposit zones to the carrier inter-deposit zones. Preferably also a position means is provide which can be unitary with the support means 600, and which stabilizes, positions and/or repositions any blurring in the printing pattern of particulate material clusters 703 towards an exact pocketing pattern prior to immobilisation. A covering means 500 and web transporting 502 provides an auxiliary layer 102, such as for instance a liquid-permeable fibrous web such as a non-woven, paper, tissue, woven, fabric, web, perforated film or foil. Alternatively the auxiliary layer 101 can also represent a homogenous and/or heterogeneous layer of glue, adhesive, binders, resins, thermoplastic material and the like, capable of sandwiching the particulate materials clusters 703 between the carrier layer and auxiliary layer to form a composite structure 700, such as for instance an absorbent structure 14. This relative expensive, technically challenging and environmentally burdensome alternative embodiment according to the invention is however not preferred above the non-woven, paper or tissue like layer for instance. A much preferred attachment process according to a preferred embodiment of the present invention comprises an airflow generated by blowing zones having an overpressure in comparison to standard process pressure and/or by suction zones having an under-pressure in comparison to standard process pressure. Alternatively, a combination of blowing and/or suction holes is used for airflow. Ultrasonic means 800 and adhesive applicator means 900 and/or 901 may also be provided.

An exemplary absorbent article is disposable baby diaper.

Figure 12:
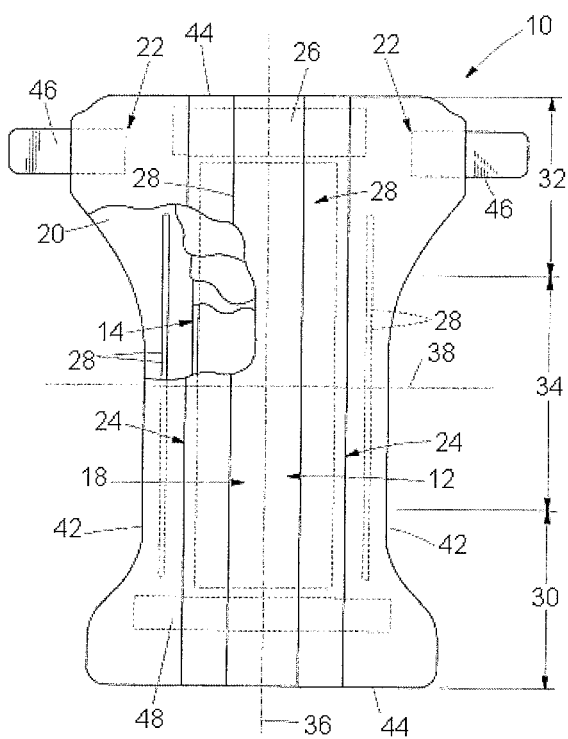
FIG. 12 is a top plan view of a diaper as a preferred embodiment of an absorbent structure according to the invention, with the upper layers partially cut away.

FIG. 12 is a top plan view of a diaper 10 as a preferred embodiment of an absorbent article including an absorbent structure according to the present invention. It should be understood, however, that the present invention is also applicable to other absorbent articles such as feminine hygiene garments, baby pants, adult incontinent garments and the like.

The absorbent article is shown in its flat out, un-contracted state with the wearer side facing the viewer. Portions of the absorbent article are cut away to more clearly show the underlying structure of the diaper 10 including the absorbent elements and absorbent components. The chassis 12 of the diaper 10 in FIG. 12 comprises the main body of the diaper 10. The chassis 12 comprises an outer covering including a liquid pervious top sheet 18 and/or a liquid impervious back sheet 20. The chassis 12 may include a portion of an absorbent structure 14 encased between the top sheet 18 and the back sheet 20. The chassis 12 may also include most or all of the absorbent structure 14 encased between the top sheet 18 and the back sheet 20. The chassis 12 preferably further includes side panels or ears 22, elasticized leg cuffs 24 and elastic waist features 26, the leg cuffs 24 and the elastic waist feature 26 each typically comprise elastic members 28. One end portion of the diaper 10 is configured as a front waist region 30 of the diaper 10. The opposite end portion is configured as a back waist region 32 of the diaper 10. An intermediate portion of the diaper 10 is configured as a crotch region 34, which extends longitudinally between the first and second waist regions 30 and 32. The waist regions 30 and 32 may include elastic elements such that they gather about the waist of the wearer to provide improved fit and containment (e.g. elastic waist feature 26). The crotch region 34 is that portion of the diaper 10 which, when the diaper 10 is worn, is generally positioned between the wearer's legs. The diaper 10 is depicted with its longitudinal axis 36 and its transverse axis 38. The periphery of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper. The chassis 12 also comprises a fastening system, which may include at least one fastening or securing member 46 and at least one landing zone 48. The various components within the diaper 10 may be bound, joined or secured by any method know in the art, for example by adhesives in uniform continuous layers, patterned layers or arrays of separate lines, spirals or spots. The top sheet 18, the back sheet 20, the absorbent structure 14 and other components may be assembled in a variety of well-known configurations and are well known in the art.

The back sheet 20 covers the absorbent structure 14 and preferably extends beyond the absorbent structure 14 toward the longitudinal edges 42 and end edges 44 of the diaper 10 and may be joined with the top sheet 18. The back sheet 20 prevents the bodily exudates absorbed by the absorbent structure 14 and contained within the diaper 10 from soiling other external articles that may contact the wearer, such as bed sheets and undergarments. In preferred embodiments, the back sheet 20 is substantially impervious to bodily exudates and comprises a laminate of a nonwoven and a thin plastic film such as a thermoplastic film. The back sheet 20 may comprise breathable materials that permit vapour to escape from the diaper 10 while still preventing bodily exudates from passing through the back sheet 20. It may be semi-rigid, non-elastic and can be made fully or partially elasticized and include backing. The back sheets 20 may be assembled in a variety of well-known configurations and are well known in the art.

The diaper 10 comprises a top sheet 18 that is preferably soft, compliant, exhibits good strikethroughs and has a reduced tendency to rewet from the liquid absorbent material. The top sheet 18 is placed in close proximity to the skin of the wearer when the diaper 10 is worn. In this way, such top sheet 18 permits bodily exudates to rapidly penetrate it so as to flow toward the absorbent structure 14 more quickly, but preferably not allowing such bodily exudates to flow back through the top sheet 18. The top sheet 18 may be constructed from any one of a wide range of liquid and vapour permeable, preferably hydrophilic, materials. The upper and lower surface of the top sheet 18 may be treated differently and may for instance include a surfactant on the upper surface so as to facilitate liquid transfer there through, especially at a central zone or area of the top sheet 18 located over the absorbent structure 10, and for instance include a hydrophobic agent on the lower surface to minimize the liquid contained within the absorbent core from contact wetting the top sheet 18 thereby reducing rewet values. The top sheet 18 may also be coated with a substance having rash preventing or rash reducing properties (e.g. aloe vera). The top sheet 18 covers substantially the entire wearer facing area of the diaper 10, including substantially all of the front waist region 30, back waist region 32, and crotch region 34. Further, the side panels 22 and/or waist feature layers of the inner region may be formed from the same single top sheet material and, thus, may be referred to as being unitary with the top sheet 18 in forming longitudinal and lateral extensions of the top sheet 18 material. Alternatively, the top sheet 18 may be formed from multiple different materials which vary across the width of the top sheet 18. Such a multiple piece design allows for creation of preferred properties and different zones of the top sheet 18. The top sheet 18 be semi-rigid, non-elastic and can be made fully or partially elasticized. The top sheet 18 may be assembled in a variety of well-known configurations and are well known in the art.

The absorbent structure 14 in FIG. 12 generally is disposed between the top sheet 18 and the back sheet 20. The absorbent structure 14 may comprise any absorbent material 110 that is generally compressible, conformable, non-irritating to the wearer's skin, and capable of absorbing and retaining bodily exudates. The absorbent structure 14 may comprise a wide variety of liquid absorbent materials 110 commonly used in absorbent articles such as fluff pulp, which is generally referred to as airlaid. Examples of other suitable absorbent materials include creped cellulose wadding; melt blown polymers; chemically stiffened, modified or cross-linked cellulosic fibres; tissue, including tissue wraps and tissue laminates; absorbent foams; absorbent sponges; absorbent polymer materials; absorbent gelling materials; or any other known absorbent materials or combinations of materials. The absorbent structure 14 may further comprise minor amounts (typically less than 10%) of non-liquid absorbent materials, such as adhesives, binders, plastics, waxes, oils and the like. The absorbent structure 14 according to various embodiments of the invention may be configured to extend substantially the full length and/or width of the diaper 10. However, alternatively the absorbent structure 14 according to the invention is not coextensive with the entire diaper 10 and is limited to certain regions of the diaper 10 such as for instance the crotch region 34. In various embodiments, the absorbent structure 14 extends to the edges of the diaper 10 and the absorbent material 110 is concentrated in the crotch region 34 or another target zone of the diaper 10. In still another embodiment, the particles can be a combination of absorbent material 110, preferably comprising absorbent polymer material, and skin care particles such as ion exchange resins, deodorant, anti-microbial agents, binder particles, or other beneficial particles.

The diaper 10 may also utilize a pair of containment walls or cuffs 24. Each cuff 24 is a longitudinally extending wall structure preferably positioned on each side of the absorbent structure 14 and spaced laterally from the longitudinal axis 36. The longitudinal ends of the cuffs 24 may be attached or joined, for example, to the top sheet 18 in the front and rear waist regions 30 and 32. Preferably, the ends of the cuffs 24 are tacked down inwardly and attached, for example, by adhesive or sonic bonding to the lower structure. Such a construction effectively biases the cuffs 24 inwardly and is generally considered to cause the cuffs 24 to exhibit improved leakage prevention properties. Preferably, the cuffs 24 are equipped with elastic members 28, which extend along a substantial length of the cuffs 24. In a common application, the elastic members 28 are placed within the cuffs 24, preferably at the top of the cuff 24 while in a stretched condition and then glued or sonic bonded to the cuff 24 at least at their ends. When released or otherwise allowed relaxing, the elastic members 28 retract inwardly. When the diaper 10 is worn, the elastic members 28 function to contract the cuffs 24 about the buttocks and the thighs of the wearer in a manner, which forms a seals between the diaper 10, the buttocks and the thighs. The cuffs 24 may be assembled in a variety of well-known configurations and are well known in the art.

The diaper 10 may also employ additional layers known in the art including an acquisition layer or surge layer, preferably situated between the top sheet and the absorbent core and highloft and/or coverstock layers. This serves to slow down the flow so that the liquid has adequate time to be absorbed by the absorbent core.

In order to keep the diaper 10 in place about the wearer, preferably at least a portion of the back waist region 32 is attached by fastening or securing members 46 to at least a portion of the front waist region 30, preferably to form leg openings and an absorbent article waist. Fastening or securing members 46 carry the tensile load around the absorbent article waist and compliment the elastic members 28 by providing a quasi-seal between the wearer, the elastic waist feature 26 and cuffs 24, so that bodily exudates are contained within the diaper 10 which are then absorbed. In other words, so that it does not leak through gaps between the wearer and the edge of the diaper 10. The fastening or securing members 46 may for instance be adhesive, mechanical fasteners, hook and loop features, conceivable strings and/or combinations thereof, i.e., anything that will secure one end of the diaper 10 to the longitudinally opposite end of the diaper 10. The fastening or securing members 46 may also be co-adhesive such that they adhere to each other but not other materials. The fastening or securing members 46 and any component thereof may include any material suitable for such a use, including but not limited to plastics, films, foams, non-woven webs, woven webs, paper, laminates, fibre reinforced plastics and the like, or combinations thereof. It may be preferable that the materials making up the fastening or securing members 46 are flexible, extensible and/or elastic, allowing them to better conform to the shape and movements of the body and thus, reduces the likelihood that the fastening system will irritate or injure the wearer's skin. Preferably, the diaper 10 is affixed to the wearer by tape fasteners which are permanently affixed to the back sheet 20. Tape fasteners are contacted with the transversely opposite side panel or ears 22 attached or joined and extending from the back sheet 20, where they remain affixed due to the binding compound applied to the fasteners. Alternatively, the absorbent article may be pants and the like. In this configuration, the absorbent article may or may not have tape fasteners. Specific disposability tapes may however also be provided on such absorbent articles. All fastening and securing elements 46 may be assembled in a variety of well-known configurations and are well known in the art.

The waist regions 30 and 32 each comprise a central region and a pair of side panels or ears 22 which typically comprise the outer lateral portions of the waist regions. These side panels 22 may be unitary with the chassis 12 and/or back sheet 20 or may be attached or joined thereto by any means know in the art. In a preferred embodiment of the present invention, the side panels 22 positioned in the back waist region 32 are flexible, extensible and/or elastic in at least the lateral direction (i.e., elasticized side panels), in another embodiment the side panels 22 are non-elastic, semi-rigid, rigid and/or stiff. These variety of side panels 22 are known in the art.

Furthermore waistbands 26 employing elastic members can be positioned along the transverse portion of the diaper 10 so that when worn, the waistbands 26 are positioned along the waist of the wearer. Generally, the waistband 26 preferably creates a seal against the waist so that bodily exudates do not leak from the regions between the elastic waistband 26 and the waist of the wearer. Although the bodily exudates are primarily absorbed by the absorbent materials within the diaper 10, the seal is important considering the assault of liquid by the wearer may overwhelm the absorption rate capacity of the absorbent structure 14. Hence, the waistbands 26 contain the liquid while it is being absorbed, they are well known in the art.

The absorbent article such as a diaper 10 may also include such other features, components and elements as are known in the art including front and rear ear panels, waist cap features, elastics and the like to provide better fit, containment and aesthetic characteristics. These features may be assembled in a variety of well-known configurations and are well known in the art.

The process for producing preferred absorbent structures in accordance with the present invention comprises the following steps: A carrier layer 101 is provided onto which absorbent material 110 is disposed by methods known in the art. To deposit the absorbent material 110, vacuum, gravity or other forces can be used. Then an auxiliary layer 102 is provided, covering the absorbent material 110, and primary bonding regions 111 and secondary bonding regions 115 are being provided. In case one would like to use adhesives or chemical binders, then it might be useful to attach these to the carrier layer 101 and/or auxiliary layer 102 layer prior to bringing the sandwich structure together. In case one opts for thermo-sealed bonding areas, then the thermo-sealing can be applied after the sandwich structure components have been brought together. It is of course also possible to combine both techniques in the same absorbent structure.

The process for producing preferred absorbent structures 14 in accordance with the present invention comprises the following steps: A carrier layer 101 is provided onto which absorbent material 110 is disposed by methods known in the art. To deposit the absorbent material 110, vacuum, gravity or other forces can be used. Then an auxiliary layer 102 is provided, covering the absorbent material 110, and primary attachments 111 and secondary attachments 115 are being provided, preferably via sonic bonding. In case one would like to use adhesives or chemical binders, then it might be useful to attach these to the carrier layer 101 and/or auxiliary layer 102 layer prior to bringing the sandwich structure together. In case one opts for thermo-sealed or sonic bonding areas, then the thermo-sealing can be applied after the sandwich structure components have been brought together. It is of course also possible to combine both techniques in the same absorbent structure.

The invention claimed is:

1. An absorbent article, wherein said absorbent article is a feminine hygiene garment, baby diaper, baby pants or adult incontinence garment, said absorbent article comprising a liquid pervious topsheet, a liquid impervious backsheet, and an absorbent structure situated in between the liquid pervious topsheet and liquid impervious backsheet;
   said absorbent structure including at least one carrier layer and at least one auxiliary layer, and absorbent material;
   wherein the carrier layer and auxiliary layer are joined via primary attachments and secondary attachments;
   wherein, apart from the primary attachments and secondary attachments, there are also unattached regions, where there is substantially no attachment, bond and/or joint between the carrier layer and auxiliary layer, thereby providing compartments in which the absorbent material is located;
   wherein the primary attachments are arranged in a primary attachment grid composed of continuous lines so as to allow for liquid distribution and transport and for a high separation force;
   wherein the primary attachment grid is designed so that in a wetted state, swollen absorbent material remains stabilized around locations where it was restrained and/or immobilized in dry state;

wherein the secondary attachments correspond with a secondary attachment pattern configured to release under swelling of the absorbent materials and/or influence of water;

wherein a plurality of the continuous lines of the primary attachment grid are substantially aligned with a longitudinal axis of the absorbent structure, and are configured to create channels and ducts which help transport fluid from a point of liquid insult to the rest of the absorbent structure via mass flow allowing better and more spread out immediate liquid management via capillary flow locally;

wherein the continuous lines are configured to guide liquid to an entire surface of the absorbent structure with the exception of outer edges thereof;

wherein the secondary attachments consist of weaker secondary attachments and stronger secondary attachments where the weaker secondary attachments are configured to loosen faster than the stronger secondary attachments.

2. The absorbent article according to claim 1, wherein the weaker and stronger secondary attachments consist of an attachment media comprising glue or hot-melt.

3. The absorbent article according to claim 1, wherein the separation force necessary to break both the weaker and the stronger secondary attachments is lower than about 5.0 N/cm.

4. The absorbent article according to claim 1, wherein absorbent material regions consist of several clusters of the absorbent material, surrounded by areas where substantially no absorbent material is present, which are configured to act as distribution and transport channels facilitating the flow of liquid away from the point of liquid insult and towards the clusters of absorbent material.

5. The absorbent article according to claim 1, wherein the weight distribution of the absorbent material over the absorbent structure is profiled, such that relative more absorbent material is concentrated near the point of liquid insult of the absorbent article.

6. The absorbent article according to claim 1, wherein weaker secondary attachments are provided at the periphery of the absorbent structure allowing for primary and easy expansion of absorbent material adjacent longitudinal and/or end edges of the absorbent structure, thereby creating containment or anti-leakage barriers within the absorbent structure, such that the weaker secondary attachment are configured to loosen and to form first barriers or embankments, whereas stronger secondary attachments are configured to form later arising secondary barriers or embankments.

7. The absorbent article according to claim 6, wherein the primary attachment grid is configured to form canals in between the first barriers or embankments and/or the secondary barriers or embankments, such that due to a time difference between the formation of the first barrier or embankments and the respective secondary barriers or embankments, the first barriers or embankments will contain liquid inside the absorbent article, where it can be distributed via the canals and it will further be stored in and contained by the secondary barriers or embankments.

8. The absorbent article according to claim 1, wherein at least 80% of the absorbent material is absorbent polymer material.

9. An absorbent article, wherein said absorbent article is a feminine hygiene garment, baby diaper, baby pants or adult incontinence garment, said absorbent article comprising a liquid pervious topsheet, a liquid impervious backsheet, and an absorbent structure situated in between the liquid pervious topsheet and liquid impervious backsheet;

said absorbent structure including at least one carrier layer and at least one auxiliary layer, and absorbent material;

wherein the carrier layer and auxiliary layer are joined via primary attachments and secondary attachments;

wherein, apart from the primary attachments and secondary attachments, there are also unattached regions, where there is substantially no attachment, bond and/or joint between the carrier layer and auxiliary layer, thereby providing compartments in which the absorbent material is located;

wherein the primary attachments are arranged in a primary attachment grid composed of continuous lines so as to allow for liquid distribution and transport and for a high separation force;

wherein the primary attachment grid is designed so that in a wetted state, swollen absorbent material remains stabilized around locations where it was restrained and/or immobilized in dry state;

wherein the secondary attachments correspond with a secondary attachment pattern configured to release under swelling of the absorbent materials and/or influence of water;

wherein the continuous lines of the primary attachment grid are configured to create channels and ducts which help transport fluid from a point of liquid contact to the rest of the absorbent structure via mass flow allowing better and more spread out immediate liquid management via capillary flow locally;

wherein the continuous lines are configured to guide liquid to an entire surface of the absorbent structure with the exception of outer edges thereof;

wherein different functionalities in between the primary attachments and secondary attachments in combination with a bonding strength differentiation in between weaker secondary attachments and stronger secondary attachments are configured for a predetermined, controlled and/or phased volume-expansion of the absorbent structure for improved fluid management.

10. An absorbent article, wherein said absorbent article is a feminine hygiene garment, baby diaper, baby pants or adult incontinence garment, said absorbent article comprising a liquid pervious topsheet, a liquid impervious backsheet, and an absorbent structure situated in between the liquid pervious topsheet and liquid impervious backsheet;

said absorbent structure including at least one carrier layer and at least one auxiliary layer, and absorbent material;

wherein the carrier layer and auxiliary layer are joined via primary attachments and secondary attachments;

wherein, apart from the primary attachments and secondary attachments, there are also unattached regions, where there is substantially no attachment, bond and/or joint between the carrier layer and auxiliary layer, thereby providing compartments in which the absorbent material is located;

wherein the primary attachments are arranged in a primary attachment grid composed of continuous lines so as to allow for liquid distribution and transport and for a high separation force;

wherein the primary attachment grid is designed so that in a wetted state, swollen absorbent material remains stabilized around locations where it was restrained and/or immobilized in dry state;

wherein the secondary attachments correspond with a secondary attachment pattern configured to release under swelling of the absorbent materials and/or influence of water;

wherein the continuous lines of the primary attachment grid are configured to create channels and ducts which help transport fluid from a point of liquid contact to the rest of the absorbent structure via mass flow allowing better and more spread out immediate liquid management via capillary flow locally;

wherein the continuous lines are configured to guide liquid to an entire surface of the absorbent structure with the exception of outer edges thereof;

wherein weaker secondary attachments are provided at the periphery of the absorbent structure allowing for primary and easy expansion of absorbent material adjacent longitudinal and/or end edges of the absorbent structure, thereby creating containment or anti-leakage barriers within the absorbent structure, such that the weaker secondary attachment are configured to loosen and to form first barriers or embankments, whereas stronger secondary attachments are configured to form later arising secondary barriers or embankments.

11. The absorbent article according to claim 10, wherein the primary attachment grid is configured to form canals in between the first barriers or embankments and/or the secondary barriers or embankments, such that due to a time difference between the formation of the first barrier or embankments and the respective secondary barriers or embankments, the first barriers or embankments will contain liquid inside the absorbent article, where it can be distributed via the canals and it will further be stored in and contained by the secondary barriers or embankments.

* * * * *